United States Patent
Kelley et al.

(10) Patent No.: US 10,772,859 B2
(45) Date of Patent: Sep. 15, 2020

(54) METHODS OF TARGETING APE/REF-1 TO INHIBIT HYPOXIA SIGNALING GENES

(71) Applicant: Indiana University Research and Technology Corporation, Indianapolis, IN (US)

(72) Inventors: Mark R. Kelley, Zionsville, IN (US); Melissa Fishel, Fishers, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/575,519

(22) PCT Filed: May 5, 2016

(86) PCT No.: PCT/US2016/030904
§ 371 (c)(1),
(2) Date: Nov. 20, 2017

(87) PCT Pub. No.: WO2016/186853
PCT Pub. Date: Nov. 24, 2016

(65) Prior Publication Data
US 2018/0200213 A1 Jul. 19, 2018

Related U.S. Application Data

(60) Provisional application No. 62/164,795, filed on May 21, 2015, provisional application No. 62/307,000, filed on Mar. 11, 2016.

(51) Int. Cl.
*A61K 31/192* (2006.01)
*A61K 45/06* (2006.01)
*A61K 31/519* (2006.01)
*A61K 31/63* (2006.01)
*A61P 35/00* (2006.01)

(52) U.S. Cl.
CPC .......... *A61K 31/192* (2013.01); *A61K 31/519* (2013.01); *A61K 31/63* (2013.01); *A61K 45/06* (2013.01); *A61P 35/00* (2018.01); *A61K 2300/00* (2013.01)

(58) Field of Classification Search
None
See application file for complete search history.

(56) References Cited

U.S. PATENT DOCUMENTS 5,210,239 A * 5/1993 Abe .................. C07C 45/00
544/176
2009/0226500 A1 9/2009 Avelar et al.

FOREIGN PATENT DOCUMENTS

| JP | 2010540544 A | 12/2010 |
| JP | 2013532158 A | 8/2013 |
| WO | 2009042542 A1 | 4/2009 |
| WO | 2013138430 A1 | 9/2013 |
| WO | 2015026818 A1 | 2/2015 |
| WO | 2015031694 A2 | 3/2015 |

OTHER PUBLICATIONS

Cardoso et al (PLOS One 7(10):e47462, 2012) (Year: 2012).*
Wu et al (Oncogene 33:173-180, 2014) (Year: 2014).*
Cardoso et al., APE1/Ref-1 Regulates STAT3 Transcriptional Activity and APE1/Ref-1-STAT3 Dual-Targeting Effectively Inhibits Pancreatic Cancer Cell Survival; PLOS/one; 2012, pp. 1-13.
SignalChem Lifesciences, SignalChem Phase 1 Clinical Trial for SLC-0111 in Solid Tumours, 2014, pp. 1-3.
Fishel et al., Impact of APE1/Ref-1 Redox Inhibition on Pancreatic Tumor Growth; Mol. Cancer Ther., 2011, vol. 10, No. 9, pp. 1698-1708.
Wang et al., S31-201, a Novel STAT3 Inhibitor, Inhibits Growth of Human Soft Tissue Sarcoma Cell Lines, World Journal of Cancer Research; 2013, vol. 1, pp. 61-68.
Zou et al., Small-molecule inhibitor of the AP endonuclease 1/REF-1 E3330 inhibits pancreatic cancer cell growth and migration; Mol Cancer Ther, 2008, vol. 7, No. 7, 10-pages.
Farid et al, Malignant Peripheral Nerve Sheath Tumors; The Oncologist; 2014, 9-pages.
Wu et al., EGFR-STAT3 signaling promotes formation of malignant peripheral nerve sheath tumors; Oncogene; 2014; vol. 33, pp. 173-180.
Kumar et al., Abstract 1769: Significant in vivo activity of an APE1/Ref-1 redox inhibitor, E3330, alone and in combination with Bevacizumab in a glioblastoma mouse model analyzed by a whole slide digital imaging system and quantitative immunohistochemistry; Cancer Research; 2012, 3-pages.
Rad et al., STAT3 and HIFIα Signaling Drives Oncogenic Cellular Phenotypes in Malignant Peripheral Nerve Sheath Tumors; Molecular Cancer Research; 2015, 13-pages.

* cited by examiner

*Primary Examiner* — Craig D Ricci
(74) *Attorney, Agent, or Firm* — Stinson LLP

(57) ABSTRACT

Methods for targeting apurinic/apyrimidinic endonuclease1/redox effector factor 1 (APE1/Ref-1) are disclosed. More particularly, methods for inhibiting APE1/Ref-1 and hypoxia-mediated signaling for decreasing survival and invasion of tumor cells exposed to hypoxic conditions are disclosed.

3 Claims, 22 Drawing Sheets

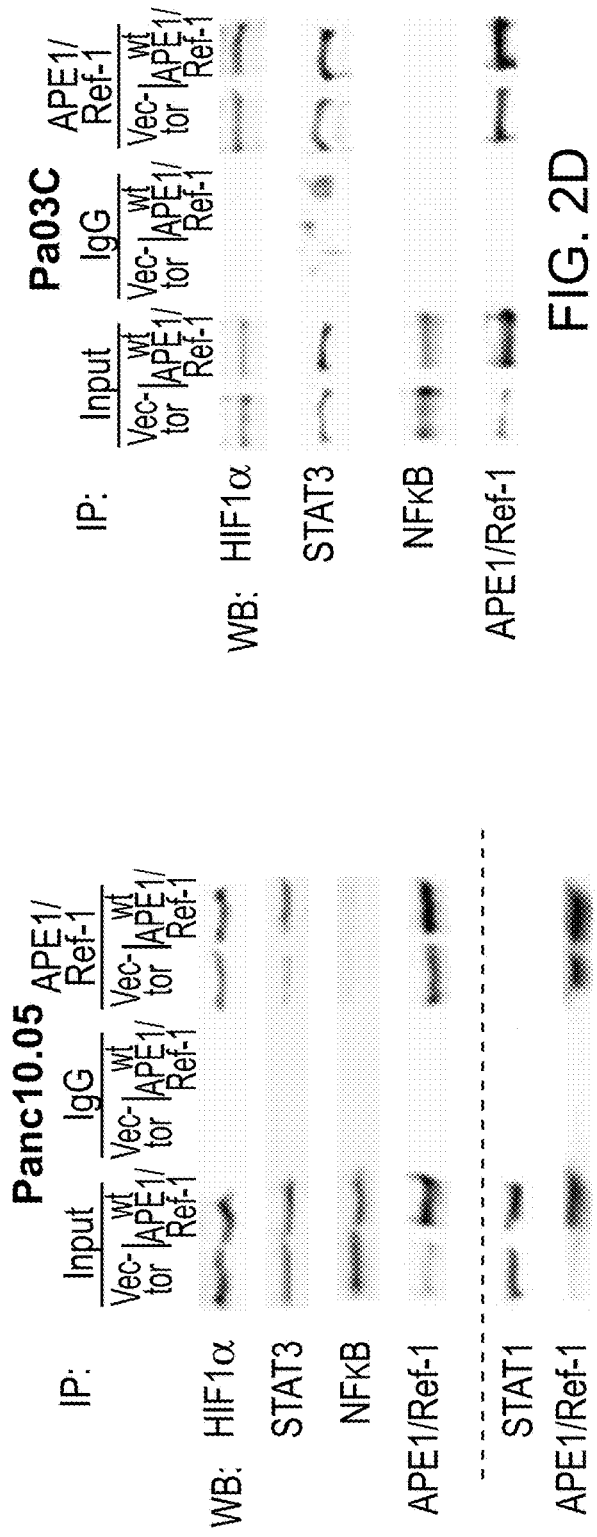
FIG. 2A
FIG. 2B
FIG. 2C
FIG. 2D

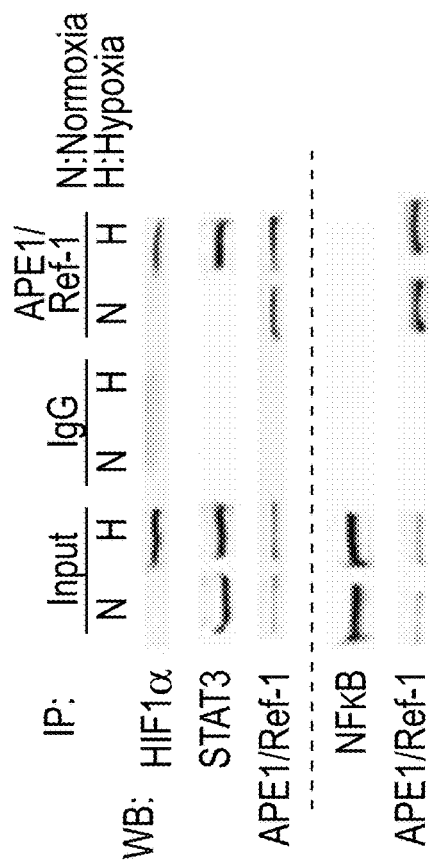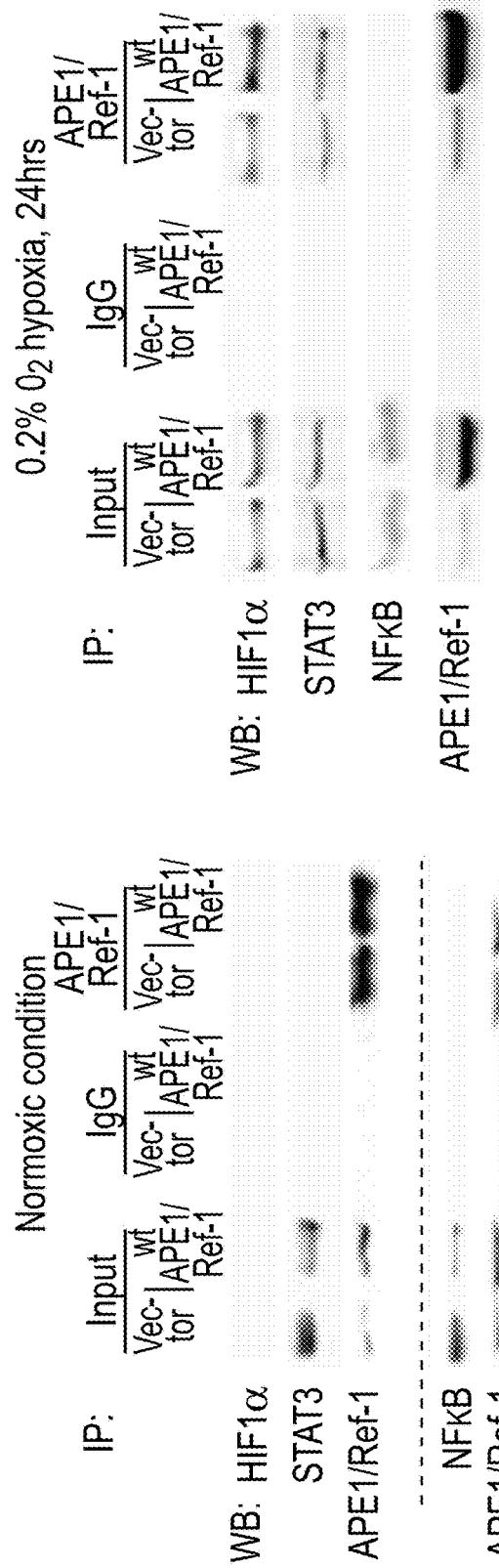
FIG. 4A
FIG. 4B
FIG. 4C

Tumor: CAFs (1:4)

Tumor: CAFs (1:4)

METHODS OF TARGETING APE/REF-1 TO INHIBIT HYPOXIA SIGNALING GENES

CROSS-REFERENCE TO RELATED APPLICATION

This application claims priority to International Application Number PCT/US2016/030904, filed on 5 May, 2016, which claims priority to U.S. Provisional Patent Application Ser. No. 62/307,000 filed March 11, 2016 and to U.S. Provisional Patent Application Ser. No. 62/164,795, filed May 21, 2015, each of which are hereby incorporated by reference in their entireties.

BACKGROUND OF THE DISCLOSURE

The present disclosure is generally directed to methods of targeting apurinic/apyrimidinic endonuclease1/redox effector factor 1 (APE1/Ref-1). More particularly, by inhibiting APE1/Ref-1, hypoxia-mediated signaling is inhibited, thereby decreasing survival and invasion of tumor cells exposed to hypoxic conditions. In one particular embodiment, the present disclosure is directed to methods of administering the combination of an inhibitor of APE1/Ref-1 and an inhibitor of carbonic anhydrase IX (CA9).

Half of all patients diagnosed with pancreatic ductal adenocarcinoma (PDAC) die within a year due to their disease. Treatment with chemotherapy has not changed the natural course of this disease. Several mechanisms are proposed to play a role in the aggressive, treatment-resistant phenotype of PDAC, including adaptation to hypoxia, which leads to increased potential for metastasis and impairs the efficacy of chemotherapy and radiotherapy. One of the main sensors of oxygen in cells is Hypoxia-Inducible Factor-1α (HIF-1α), a transcription factor that is rapidly degraded under normoxic conditions, but upregulates a number of genes under hypoxic conditions that contribute to survival, metastasis, and angiogenic signaling in the tumor microenvironment. One of the most notable HIF targets is carbonic anhydrase IX (CA9), which promotes tumor cell survival and metastasis by maintaining a steady intracellular pH while acidifying the microenvironment, thereby encouraging epithelial-mesenchymal transition and contributing to extracellular matrix degradation.

Apurinic/apyrimidinic endonuclease1/redox effector factor 1 (APE1/Ref-1) is a multi-function protein that possesses a DNA repair function in base excision repair, as well as the ability to reduce transcription factors and enable them to bind to their DNA target sequences. APE1/Ref-1 regulates several transcription factors involved in preventing apoptosis, survival mechanisms, and hypoxia signaling, including HIF-1α.

Based on the foregoing, the present disclosure is directed to interfering with APE-1/Ref-1 to further interfere with HIF-1α-mediated signaling, leading to a decreased survival and invasion of tumor cells exposed to hypoxic conditions.

BRIEF DESCRIPTION OF THE DISCLOSURE

The present disclosure is generally directed to methods of targeting apurinic/apyrimidinic endonuclease1/redox effector factor 1 (APE1/Ref-1). More particularly, by inhibiting APE1/Ref-1, hypoxia-mediated signaling is inhibited, thereby decreasing survival and invasion of tumor cells exposed to hypoxic conditions.

Accordingly, in one aspect, the present disclosure is directed to a method for inhibiting hypoxia signaling genes in a subject in need thereof. The method comprises administering to the subject an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1.

In another aspect, the present disclosure is directed to a method for inhibiting pancreatic ductal adenocarcinoma (PDAC) in a subject in need thereof. The method comprises administering to the subject an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1.

In yet another aspect, the present disclosure is directed to a method for inhibiting cancer cell growth in a subject in need thereof. The method comprises administering to the subject an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1, and administering at least one additional therapeutic agent to the subject. In one particular embodiment, the subject has pancreatic ductal adenocarcinoma (PDAC). In another embodiment, the subject has malignant peripheral nerve sheath tumors (MPNST) (also called schwannomas, or sarcoma and can be associated with a form of neurofibrosarcoma (NF1)).

In yet another aspect, the present disclosure is directed to a method for inhibiting malignant peripheral nerve sheath tumors (MPNST) in a subject in need thereof. The method comprises administering to the subject an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 2A-2D depict the presence of HIF1α, STAT3, and NFκB in cells lines and the interaction of APE1/Ref-1 with STAT3 and HIF1α under hypoxic conditions as analyzed in Example 1. Particularly, APE1/Ref-1 interactions with HIF1α and STAT3 are stimulated by hypoxia in PDAC cells. Panc10.05 (FIG. 2A) and Pa03C (FIG. 2B) cells were incubated under normal or hypoxic (0.2% oxygen) conditions for 24 hours prior to collection and immunoprecipitation of endogenously expressed APE1/Ref-1. Stable cell lines overexpressing APE1/Ref-1 were generated using wt-APE/Lenti-CMV-GFP and compared to Lenti-CMV-GFP, "vector" (FIG. 2C: 10.05; FIG. 2D: Pa03C), and APE1/Ref-1 immunoprecipitation was performed following exposure to 0.2% oxygen for 24 hours. Western analyses of the IPs with HIF1α, STAT3, APE1/Ref-1, NFκB, and STAT1 antibodies were performed.

FIGS. 4A-4C show that APE1/Ref-1 interactions with HIF1α and STAT3 are stimulated by hypoxia in Cancer-Associated Fibroblast (CAF) cells. Particularly, UH1303-02 hTERT (CAF) cells were incubated under normoxic or hypoxic (0.2% oxygen) for 24 hours prior to collection and immunoprecipitation of endogenously expressed APE1/Ref-1 (FIG. 4A). Stable cell lines overexpressing APE1/Ref-1 were generated using wt-APE/Lenti-CMV-GFP (vs. Lenti-CMV-GFP, "vector") (FIGS. 4B & 4C), and APE1/Ref-1 immunoprecipitation was performed following incubation in normoxia (FIG. 4B) or 0.2% oxygen (FIG. 4C) for 24 hours. Western analyses of the IPs with HIF1α, STAT3, APE1/Ref-1, and NFκB antibodies were performed.

(FIGS. 11B & 11C) or Pei et al. (11D).

FIG. 18A depicts the scratched area over time. Scale bar represents 250 µm/cells imaged on a microscope at ×10 magnification. FIG. 18B is a graph depicting percentage of migrated cells.

FIG. 19A depicts the scratched area over time. Scale bar represents 250 µm/cells imaged on a microscope at ×10 magnification. FIG. 19B is a graph depicting percentage of migrated cells.

DETAILED DESCRIPTION OF THE DISCLOSURE

Figure 1:
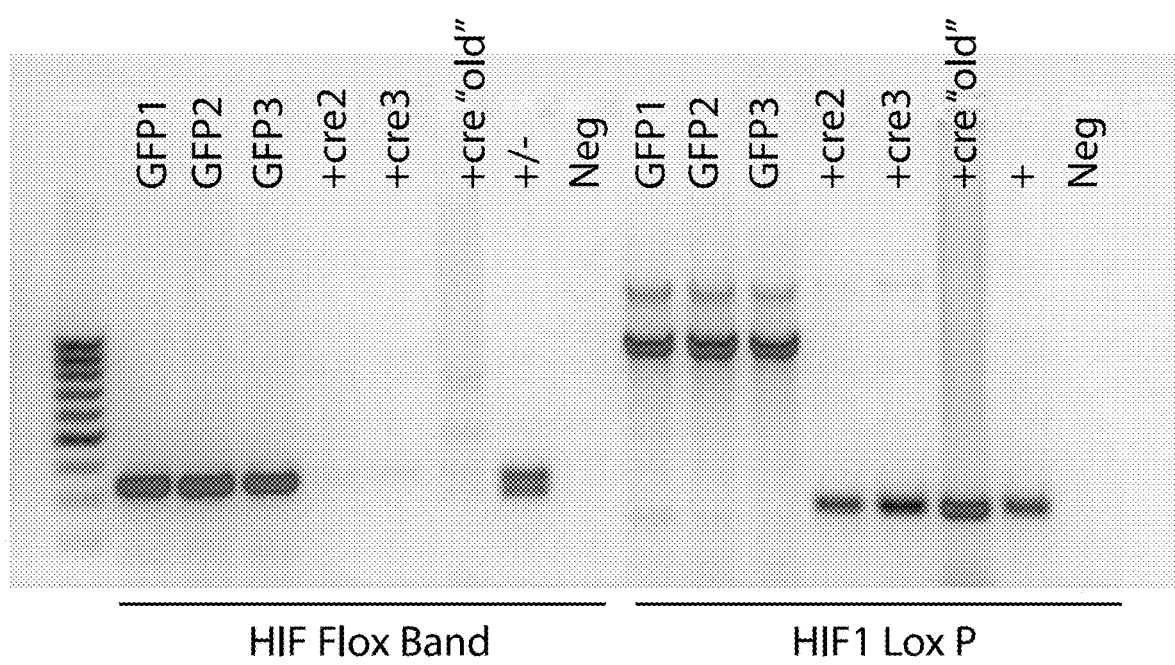
FIG. 1 depicts the deletion of HIF in the HIF-1-/- MEF Generation prepared in Example 1. 2-loxP/1-loxP PCR was performed using DNA collected from HIF-1-floxed mouse embryonic fibroblast (MEF) cells transduced with either Ad-CMV-Cre (Cre adenovirus) or Ad-GFP (control) vector.

Unless otherwise defined, all terms of art, notations and other scientific terminology used herein are intended to have the ordinary meanings commonly understood by those of ordinary skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

A. Definitions

As used herein, the term "sample" refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. A "tissue" or "cell sample" refers to a collection of similar cells obtained from a tissue of a subject or patient. The source of the tissue or cell sample may be blood or any blood constituents (e.g., whole blood, plasma, serum) from the subject. The tissue sample can also be primary or cultured cells or cell lines. Optionally, the tissue or cell sample is obtained from a diseased tissue/organ. The tissue sample can contain compounds which are not naturally intermixed with the tissue in nature such as preservatives, anticoagulants, buffers, fixatives, nutrients, antibiotics, and the like.

As used herein, the terms "control", "control cohort", "reference sample", "reference cell", "reference tissue", "control sample", "control cell", and "control tissue" refer to a sample, cell or tissue obtained from a source that is known, or believed, to not be afflicted with the disease or condition for which a method or composition of the present disclosure is being used to identify. The control can include one control or multiple controls. In one embodiment, a reference sample, reference cell, reference tissue, control sample, control cell, or control tissue is obtained from a healthy part of the body of the same subject or patient in whom a disease or condition is being identified using a composition or method of the present disclosure. In one embodiment, a reference sample, reference cell, reference tissue, control sample, control cell, or control tissue is obtained from a healthy part of the body of an individual who is not the subject or patient in whom a disease or condition is being identified using a composition or method of the invention.

The term "subject" is used interchangeably herein with "patient" to refer to an individual to be treated. The subject is a mammal (e.g., human, non-human primate, rat, mouse, cow, horse, pig, sheep, goat, dog, cat, etc.). The subject can be a clinical patient, a clinical trial volunteer, an experimental animal, etc. The subject can be suspected of having or at risk for having a condition (such as PDAC or MPNST) or be diagnosed with a condition (such as PDAC or MPNST). The subject can also be suspected of having or at risk for having PDAC, MPNST, renal cancer, and bladder cancer. According to one embodiment, the subject to be treated according to this invention is a human.

The term "inhibit", and derivates thereof, includes its generally accepted meaning, which includes reducing, prohibiting, preventing, restraining, and slowing, stopping, or reversing progression or severity. Thus, the present methods include both medical therapeutic and prophylactic administration, as appropriate. As such, a subject in need thereof, as it relates to the therapeutic uses herein, is one identified to require or desire medical intervention.

An "effective amount" is that amount of an agent necessary to inhibit the pathological diseases and disorders herein described. When at least one additional therapeutic agent is administered to a subject, such agents may be administered sequentially, concurrently, or simultaneously, in order to obtain the benefits of the agents.

As used herein, "treating", "treatment", "alleviating", "alleviate", and "alleviation" refer to measures, wherein the object is to prevent or slow down (lessen) the targeted pathologic condition or disorder or relieve some of the symptoms of the disorder. Those in need of treatment can include those already with the disorder as well as those prone to have the disorder, those at risk for having the disorder and those in whom the disorder is to be prevented.

Hypoxic conditions in many tumors (e.g., pancreatic tumors, brain, ovarian, bladder, renal, prostate and sarcomas) are associated with poor prognosis. Oxygen deprivation leads to stabilization of hypoxia inducible factor 1 alpha (HIF1α), a transcription factor that upregulates a variety of factors that contribute to increased drug resistance, proliferation, and migration/invasion in tumor cells. HIF-1 transcriptional activity depends on stabilization of its a subunit, which is targeted for degradation under normoxic conditions by proline hydroxylation and subsequent von Hippel-Lindau protein (VHL)-mediated ubiquitination. Stable HIF1α dimerizes with the constitutively expressed β subunit to activate genes with hypoxia-response elements (HREs) in their promoters. No HIF-1-specific inhibitors currently exist, so targeting its vital transcriptional targets and the enzymes that regulate HIF-1 activity are promising ways to modulate hypoxia signaling in cancer cells.

The present disclosure generally relates to methods of targeting apurinic/apyrimidinic endonuclease1/redox effector factor 1 (APE1/Ref-1). More particularly, by inhibiting APE1/Ref-1, hypoxia-mediated signaling is inhibited, thereby decreasing survival and invasion of tumor cells exposed to hypoxic conditions. In one particular embodiment, the present disclosure is directed to methods of administering an inhibitor of APE1/Ref-1 and an additional therapeutic agent. As shown in the Examples, upon blockade of multiple hypoxia signaling pathways with an inhibitor of APE1/Ref-1 and an additional therapeutic agent, tumor growth is dramatically reduced, even in the presence of cancer-associated fibroblasts (CAFs).

The redox function of Ape1/Ref-1 was found to be selectively inhibited by 3-[(5-(2,3-dimethoxy-6-methyl1,4-benzoquinoyl)]-2-nonyl-2-proprionic acid, below (hereinafter "E3330" or "3330" or "APX3330"). Further information on APX3330 may be found in Abe et al., U.S. Pat. No. 5,210,239, incorporated herein by reference to the extent it is consistent herewith.

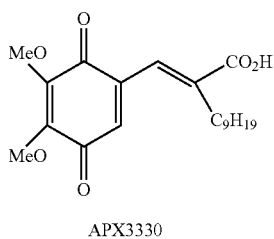

APX3330

Interestingly, the Examples below indicate that selective blocking of the redox function of Ape1/Ref-1 does not cause any or any appreciable apoptosis in normal cells. One very well might expect that the selective blocking resulting in increased apoptosis in cancerous cells would also impair normal cells. However, this was found not to be the case.

Where subject applications are contemplated, particularly in humans, it will be necessary to prepare pharmaceutical compositions in a form appropriate for the intended application. Generally, this will entail preparing compositions that are essentially free of impurities that could be harmful to a subject.

The agents can be administered orally, intravenously, intramuscularly, intrapleurally or intraperitoneally at doses based on the body weight and degree of disease progression of the subject, and may be given in one, two or even four daily administrations.

One will generally desire to employ appropriate salts and buffers to render agents stable and allow for uptake by target cells. Aqueous compositions of the present disclosure comprise an effective amount of the agent, dissolved or dispersed in a pharmaceutically acceptable carrier or aqueous medium. Such compositions also are referred to as innocuously. The phrase "pharmaceutically" or "pharmacologically acceptable" refers to molecular entities and compositions that do not produce adverse, allergic, or other untoward reactions when administered to a subject. As used herein, pharmaceutically acceptable carrier includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Compositions for use in the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, as described herein.

For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In some particularly suitable embodiments, the form is sterile and is fluid to the extent that easy administration via syringe exists. It can be stable under the conditions of manufacture and storage and can be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration agents of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions for use in the present disclosure may be formulated in a neutral or salt form. Pharmaceutically acceptable salts include the acid addition salts (formed with the free amino groups of the protein), which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, general safety and purity standards as required by FDA and foreign counterpart agencies.

In some aspects, as noted above, the APE1/Ref-1 inhibitor is administered in combination with one or more additional therapeutic agents. Exemplary additional therapeutic agents include an inhibitor of signal transducer and activator of transcription 3 (STATS) (e.g., 2-Hydroxy-4-(((4-methylphenyl)sulfonyloxy)acetyl)amino)-benzoic acid/S3I-201, 6-Nitrobenzo[b]thiophene-1,1-dioxide/stattic, OCHROMYCINONE, 4-[[(4-cyclohexylphenyl)methyl][2-[methyl[(2,3,4,5,6-pentafluorophenyl)sulfonyl]amino]acetyl]amino]-benzoic acid (SH-4-54), 4-(N-(4-Cyclohexylbenzyl)-2-(2,3,4,5,6-pentafluoro-N-methylphenyl)sulfonamido)acetamido)-2-hydroxybenzoic acid (BP-1-102), as well as other inhibitors based on the BP-1-102 structure (e.g., PG-S3-001, PG-S2-002 and PG-S3-003 described in Karan et al., Mol. Cancer Ther. 2016 Feb. 12., pii: molcanther.0003.2015 (structures shown below), and DR-4-89)), an inhibitor of carbonic anhydrase IX (CA9), an inhibitor of vascular endothelial growth factor (VEGF) and/or inhibitor of VEGF receptor (VEGF-R) (e.g., AVASTIN®/bevacizumab (VEGF antibody inhibitor), ZALTRAP®/ziv-aflibercept, CEDIRANIB®/AZD-2171 (Recentin) (VEGF-R inhibitor), VOTRIENT®/pazopanib/GW786034 (VEGF-R inhibitor), NEVAXAR®/sorafenib (VEGF-R inhibitor), SUTENT®/sunitinib malate (VEGF-R inhibitor), CYRAMZA®/ramucirumab (VEGF-R inhibitor), and STIVARGA®/regorafenib) (VEGF-R inhibitor), an inhibitor of Janus kinase (JAK) (e.g., Ruxolitinib ("RUX"), Erlotinib, LY3009104, Tofacitibnib, Baricitinib, CYT387, Filgotinib, Lestaurtinib, Pacritinib), and combinations thereof.

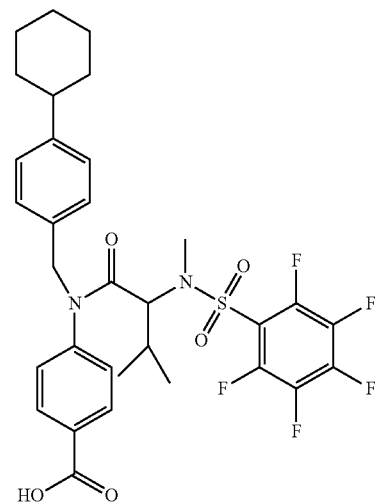

PG-S3-001

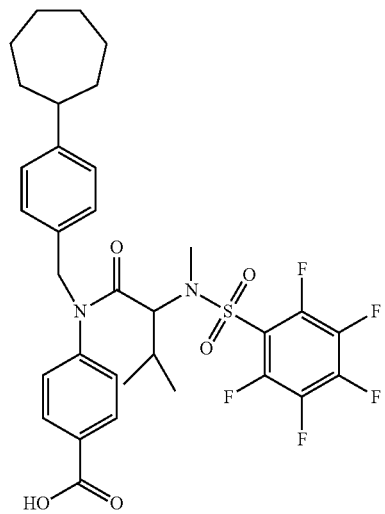

PG-S3-002

-continued

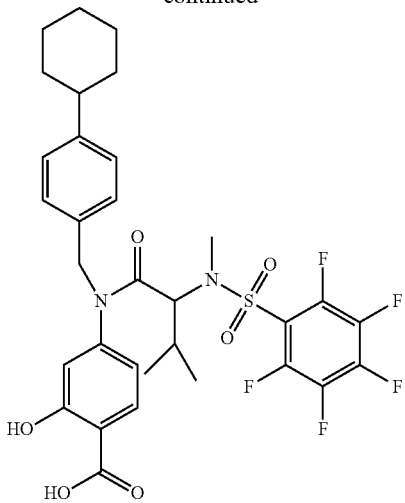

PG-S3-003

In one particularly suitable embodiment, the additional therapeutic agent is a carbonic anhydrase IX (CA9) inhibitor. Exemplary CA9 inhibitors include SLC-0111 (SignalChem Lifesciences Corp., Richmond, British Columbia) and its analog, FC13-555A. The structures of SLC-0111 and FC13-555A are shown below:

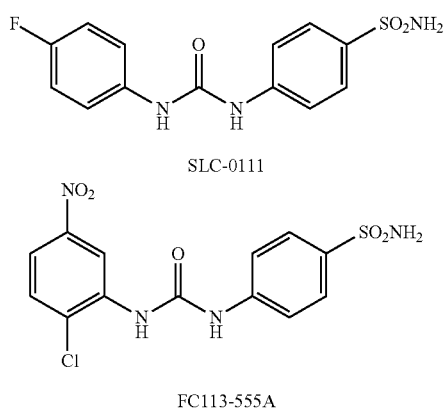

In another particularly suitable embodiment, the additional therapeutic agent is a Janus kinase (JAK) inhibitor, particularly interfering with the JAK-STAT signaling pathway. Exemplary JAK inhibitors include Ruxolitinib (JAK1/JAK2 inhibitor), Erlotinib (JAK2 inhibitor), LY3009104 (JAK2 inhibitor), Tofacitibnib (JAK3 inhibitor), Baricitinib (JAK1/JAK2 inhibitor), CYT387 (JAK2 inhibitor), Filgotinib (JAK1 inhibitor), Lestaurtinib (JAK2 inhibitor), Pacritinib (JAK2 inhibitor), and combinations thereof.

It has now been found that knockdown of APE1/Ref-1 protein diminishes HIF-mediated transcription and HIF-1α-induced downstream targets including CA9 and angiopoietin-like 4 (ANGPTL4). Particularly, HIF-1α is a critical factor in hypoxia-induced CA9 transcription, as well as STAT5. CA9 functions as part of the cellular response to hypoxia to regulate intracellular pH to promote cell survival. It is now been found that by blocking both CA9 activity and CA9 transcription via APE1/Ref-1, the decreased PDAC cell proliferation under hypoxia conditions is seen.

While described herein with respect to PDAC, it should be recognized that the methods of the present disclosure can be used to inhibit hypoxia-mediated signaling, thereby decreasing survival and invasion of tumor cells exposed to hypoxic conditions, other than in PDAC. In particular, the methods can be used to inhibit brain cancer, ovarian cancer, bladder cancer, renal cancer, prostate cancer, sarcomas, Malignant Peripheral Nerve Sheath Tumors (MPNST), and the like.

The present disclosure uses examples to disclose the invention and also to enable any person skilled in the art to practice the invention, including making and using any panels or devices and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Example 1

In this Example, the mechanisms by which APE1/Ref-1 regulates hypoxia signaling through HIF1α-mediated transcription are analyzed. Further, the effects of combination treatment with an APE1/Ref-1 inhibitor and CA9 inhibitor on tumor size and proliferation are also analyzed.

Methods and Materials

Cell Culture: Cells were maintained in culture as described in Jiang, Zhou et al. (2010) Cancer Investigation 28(9): 885-895; Fishel, Jiang et al. (2011) Molecular Cancer Therapeutics 10(9): 1698-1708; Cardoso, Jiang et al. (2012) PLoS ONE 10: e47462, Fishel, Wu et al. (2015) J Biol Chem 290(5): 3057-3068. Patient-derived tumor cells and CAF19 cells were from Dr. Anirban Maitra's lab (The Johns Hopkins University) (Jones, Zhang et al. 2008). Cancer-associated fibroblasts, UH1303-02 were isolated using the outgrowth method from patient tumor tissue as described in Walter, Omura et al. (2008) Cancer Biol Ther 7(6): 882-888. All cell lines were authenticated via STR analysis (IDEXX BioResearch) and checked routinely for *mycoplasma* contamination. Hypoxia exposure was achieved using a Ruskinn Invivo$_2$ 200 hypoxia work station. CMV-EGFP-WT APE1/Ref-1 and CMV-EGFP lentiviral constructs were used to overexpress APE1/Ref-1 as described in Kim, Guo et al. (2015) Mutat Res 779: 96-104. To detect the cells for imaging, a CMV-EGFP lentiviral construct was used. Additionally, 150 pfu/cell of the pCL7TdTOMwo lentiviral vector was incubated with Pa03C and Panc10.05 cells for 48 hours to make cells stably express TdTomato.

Western Blot Analysis: Western blots were performed as described in Wang, Luo et al. (2004) Mol Cancer Ther 3(6): 679-686; Fishel, He et al. (2008) DNA Repair (Amst) 7(2): 177-186; Fishel, Colvin et al. (2010) Hematol 38(12): 1178-1188; Jiang, Zhou et al. (2010) Cancer Investigation 28(9): 885-895; Fishel, Jiang et al. (2011) Molecular Cancer Therapeutics 10(9): 1698-1708; Cardoso, Jiang et al. (2012) PLoS ONE 10: e47462; Fishel, Wu et al. (2015) J Biol Chem 290(5): 3057-3068, with antibodies for APE1/Ref-1 (Novus Biologicals; Littleton, Colo.), HIF1α (GeneTex; Irvine, Calif.), STAT1, STAT5, (Cell Signaling; Danvers, Mass.), NFκB (abcam; Cambridge, Mass.), CA9 (Santa Cruz; Dallas, Tex.) and Vinculin (Sigma; St. Louis, Mo.).

Co-immunoprecipitation: Samples were co-immunoprecipitated using the Pierce Co-IP kit (Thermo Scientific) with modifications as described in Fishel, Wu et al. (2015) J Biol Chem 290(5): 3057-3068.

Transfection: PDAC and CAF cells were transfected with APE1/Ref-1 siRNA as described in Wang, Luo et al. (2004) Mol Cancer Ther 3(6): 679-686; Fishel, He et al. (2008) DNA Repair (Amst) 7(2): 177-186; Fishel, Colvin et al. (2010) Hematol 38(12): 1178-1188; Jiang, Zhou et al. (2010) Cancer Investigation 28(9): 885-895; Fishel, Jiang et al. (2011) Molecular Cancer Therapeutics 10(9): 1698-1708; Cardoso, Jiang et al. (2012) PLoS ONE 10: e47462; Fishel, Wu et al. (2015) J Biol Chem 290(5): 3057-3068. siRNAs used were: #1 or scrambled control (previously reported) and two LifeTech validated siRNAs (#2, s1445 and #4, s1447) (Fishel, Wu et al. (2015) J Biol Chem 290(5): 3057-3068). APE1/Ref-1 siRNA #1 was used as the standard siRNA unless otherwise specified.

Transient Luciferase Reporter Assays: MIA PaCa-2 cells were co-transfected with constructs containing luciferase driven by HIF1α and a Renilla luciferase control reporter vector as described in Luo, Delaplane et al. (2008) Antioxid Redox Signal 10(11): 1853-1867; Fishel, Wu et al. (2015) J Biol Chem 290(5): 3057-3068 using X-tremeGENE 9 DNA transfection reagent (Roche, Indianapolis, Ind.) along with siRNA as described above. Firefly and Renilla luciferase activities were assayed by using the Dual Luciferase Reporter Assay System (Promega Corp.) as before (Luo, Delaplane et al. (2008) Antioxid Redox Signal 10(11): 1853-1867; Cardoso, Jiang et al. (2012) PLoS ONE 10: e47462; Fishel, Wu et al. (2015) J Biol Chem 290(5): 3057-3068).

qRT-PCR Reactions: qRT-PCR was used to measure the mRNA expression levels of CA9 as described in Fishel, Jiang et al. (2011) Molecular Cancer Therapeutics 10(9): 1698-1708. Cells were treated with APE1/Ref-1 siRNA or increasing amounts of APX3330 in the presence or absence of hypoxia (1% and 0.2% $O_2$) for 24 hours, then total RNA was extracted from cells using the QiagenRNeasy Mini kit (Valencia, Calif.). First-strand cDNA synthesis and quantitative PCR were performed as described in Fishel, Vasko et al. (2007) Mutat Res 614(1-2): 24-36; Jiang, Guo et al. (2009) DNA Repair (Amst) 8(11): 1273-1282; Fishel, Jiang et al. (2011) Molecular Cancer Therapeutics 10(9): 1698-1708. The relative quantitative mRNA level was determined using the comparative Ct method using 18S rRNA, RPLPO, and B2M as reference genes (Livak and Schmittgen (2001) Methods 25(4): 402-408; Fishel, Vasko et al. (2007) Mutat Res 614(1-2): 24-36; Jiang, Guo et al. (2009) DNA Repair (Amst) 8(11): 1273-1282). The primers for CA9, 18S, RPLPO, and B2M are commercially available (Applied Biosystems).

Inhibitors: Compounds were prepared and used as previously described: APX3330 (Luo, Delaplane et al. (2008) Antioxid Redox Signal 10(11): 1853-1867; Fishel, Colvin et al. (2010) Exp Hematol 38(12): 1178-1188; Nyland, Luo et al. (2010) J Med Chem 53(3): 1200-1210; Su, Delaplane et al. (2011) Biochemistry 50: 82-92) and SLC-0111 (ClinicalTrials.gov, Nishimori, Minakuchi et al. (2006) J Med Chem 49(6): 2117-2126; Pacchiano, Aggarwal et al. (2010) Chem Commun (Camb) 46(44): 8371-8373; Lou, McDonald et al. (2011) Cancer Res 71(9): 3364-3376; Pacchiano, Carta et al. (2011) J Med Chem 54(6): 1896-1902; McDonald, Winum et al. (2012) Oncotarget 3(1): 84-97; Supuran (2015) J Enzyme Inhib Med Chem: 1-16; Supuran and Winum (2015) Expert Opin Drug Discov 10(6): 591-597). Additionally, the SLC-0111 analog, FC13-555A, was synthesized as described below.

Synthesis of 4-[3-(2-chloro-5-nitro-phenyl)-ureido]-benzenesulfonamide FC13-555A

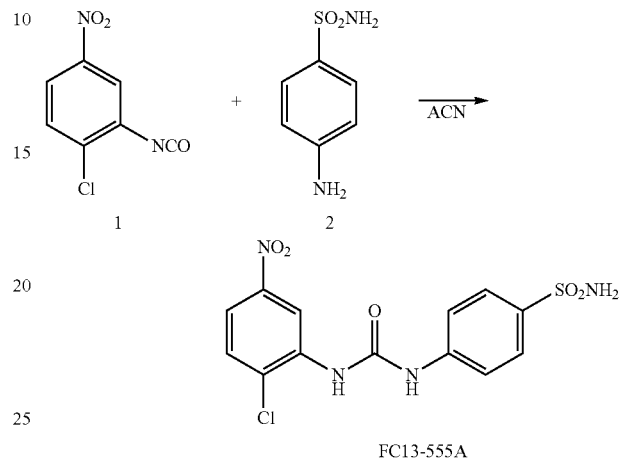

FC13-555A

1-Chloro-2-isocyanato-4-nitro-benzene 1 (1.0 eq) was added to a solution of sulphanilamide 2 (1.0 eq) in ACN. The solution was stirred at room temperature for 3 hours and a white precipitate was formed which was collected by filtration, triturated with diethyl ether and dried under vacuo to afford the title compound as a pale yellow solid.

4-[3-(2-Chloro-5-nitro-phenyl)-ureido]-benzenesulfonamide FC13-555A: 89% yield; silica gel TLC $R_f$ 0.28 (Ethyl acetate/n-hexane 30% v/v); $\delta_H$ (400 MHz, DMSO-$d_6$) 7.28 (2H, brs, exchange with $D_2O$, $SO_2NH_2$), 7.78 (2H, d, J 8.8, ArH), 7.83 (3H, m, ArH), 7.94 (2H, d, J 8.8, ArH), 8.82 (1H, brs, exchange with $D_2O$, NH), 9.21 (1H, s, ArH), 10.00 (1H, s; ArH); $\delta_C$ (100 MHz, DMSO-$d_6$) 115.6, 118.5, 118.8, 127.8, 128.9, 131.3, 137.7, 138.6, 142.9, 147.5, 152.7; m/z (ESI-MS-positive) 371.01 (M+H); Anal. Calc: C, 42.11; H, 2.99; S, 8.65; Anal. Found. C, 42.15; H, 3.04; S, 8.62.

Cell Proliferation: PDAC cell proliferation in monolayer was measured using the Alamar Blue assay as described in Fishel, Wu et al. (2015) J Biol Chem 290(5): 3057-3068. Cells treated with APX3330 and SLC-0111 were exposed to hypoxia for six days followed by addition of Alamar Blue reagent (Invitrogen) and subsequent fluorescence analysis. Fold change refers to the fluorescence reading for cells treated with indicated inhibitors compared to cells growing in normal media.

pH Assay: Intracellular pH was evaluated using the pHrodo Red AM Intracellular pH Indicator (LifeTech). PDAC cells treated with APX3330 and SLC-0111 were exposed to hypoxia for 48 hours followed by analysis with pHrodo Red AM dye. Intracellular pH Calibration Buffers (LifeTech) were used to create a standard curve of fluorescence intensity for determination of pH values. Results were normalized to MTS analysis to account for changes in proliferation.

Statistical Analysis. qPCR data points for scrambled, siAPE1/Ref-1, and hypoxia treatments were analyzed using the $2^{-\Delta\Delta C_T}$ method and analysis of covariance (ANCOVA) models as described in Yuan, Reed et al. (2006) BMC Bioinformatics 7: 85; Fishel, Wu et al. (2015) J Biol Chem 290(5): 3057-3068. Data points in tests with multiple treatment groups were analyzed using post-hoc Multiple Comparisons Tests (Tukey, Dunnett or Sidak, as appropriate). For evaluation of data curves using multiple drugs, an extra-sum-of-squares F test was used to compare the goodness-of-fit of a nonlinear regression curve shared between groups with that of separate curves for each group. Differences between the treatment groups and control group were considered significant if p<0.05 following Bonferroni corrections as appropriate. Statistical analyses were performed using SAS (Version 9.3, Copyright©2010 SAS Institute Inc. Cary, N.C.) and Prism (Version 6.0f, Copyright ©2014 GraphPad Software Inc. La Jolla, Calif.).

HIF-1-/- MEF Generation: HIF-1-floxed mouse embryonic fibroblast (MEF) cells were transduced with Ad-CMV-Cre (Cre adenovirus) or Ad-GFP (control) vector (Vector BioLabs; Malvern, Pa.) for 24 hours using 5 ng/mL polybrene to produce HIF-1-deficient cells (Attardi, Lowe et al. (1996) Embo j 15(14): 3693-3701; Rankin, Wu et al. (2012) Cell 149(1): 63-74). PCR was used to verify the deletion of HIF (FIG. 1).

3D Co-Cultures: Ultra low attachment 96-well plates (Corning Inc., Life Sciences) were used to generate 3-dimensional tumor spheroids in the presence and absence of CAFs (75 µL/well) as described previously (Sempere, Gunn et al. (2011) Cancer Biol Ther 12(3): 198-207; Arpin, Mac et al. (2015) Molecular Cancer Therapeutics). Cells were stably transduced with EGFP (green) or TdTomato (red) as indicated to preserve the genetic characteristics of the low passage patient cells (Jones, Zhang et al. (2008) Science 321(5897): 1801-1806). Cells were re-suspended in colorless DMEM growth media containing 3% Reduced Growth Factor Matrigel (RGF, BD Biosciences) and 5% FBS. Following plating, cells were treated on Days 4 and 8 with media containing 5% serum, 3% RGF Matrigel, and inhibitors as indicated. On Day 12, spheroids were analyzed using Thermo ArrayScan high-content imaging system (Lovborg, Nygren et al. (2004) Mol Cancer Ther 3(5): 521-526; Lindblom, Berg et al. (2012) Toxicol Pathol 40(1): 18-32). Images of 3D structures were captured by ArrayScan using a 2.5× objective for TdTomato and EGFP; then 2D projections were processed to quantify differences in total intensity and total area of both CAFs and tumor.

Results

APE1/Ref-1 Interactions with HIF1α and STAT3 are Stimulated by Hypoxia

Figure 3A:
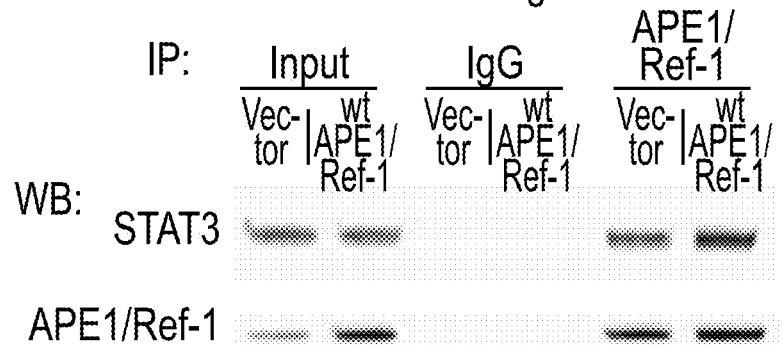
FIGS. 3A & 3B depict interactions between APE1/Ref-1 and the transcription factors in cells treated with TNFα or IL-6 under normoxic conditions. Stable Panc10.05 cell lines overexpressing APE1/Ref-1 (wt-APE/Lenti-CMV-GFP vs. Lenti-CMV-GFP, "vector") were exposed to IL-6 (FIG. 3A) or TNFα (FIG. 3B) for the times indicated, and APE1/Ref-1 was immunoprecipitated. Western analyses of the IPs with STAT3, APE1/Ref-1, and NFκB antibodies were performed.
Figure 3B:
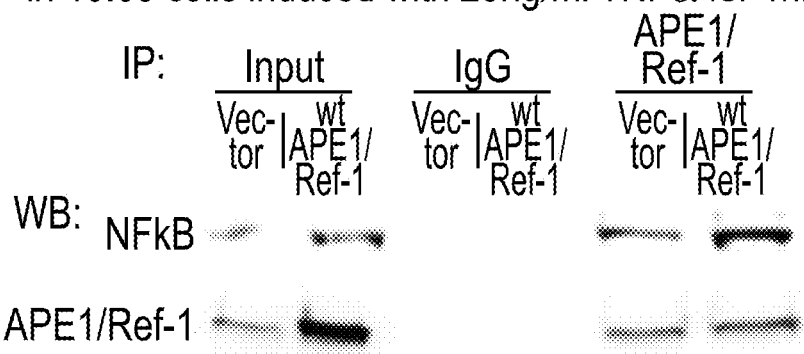

Previously published data demonstrated that decreased STAT3, HIF1α, and NFκB activity followed knockdown of APE1/Ref-1 and/or inhibition of APE1/Ref-1 redox signaling with the selective inhibitor APX3330 (also called APX3330) (Fishel, Jiang et al. (2011) Molecular Cancer Therapeutics 10(9): 1698-1708; Cardoso, Jiang et al. (2012) PLoS ONE 10: e47462). Similarly, it was found that inhibition of APE1/Ref-1 led to a decrease in a major HIF-1 target within cells, Carbonic Anhydrase IX (CA9). To further dissect the role of APE1/Ref-1 in hypoxia signaling and more clearly determine whether hypoxia stimulates interactions between APE1/Ref-1 and its redox targets, endogenous APE1/Ref-1 was immunoprecipitated from lysates of two low passage PDAC cell lines (Panc10.05 and Pa03C) under normoxic and hypoxic (0.2% $O_2$) conditions. IPs were probed for HIF1α, STAT3, and NFκB. HIF1α and STAT3, but not NFκB, were detected in the pull-down fractions under hypoxic conditions, but these interactions were not detected under normoxic conditions (FIGS. 2A & 2B). Controls of TNFα (NFκB) and IL-6 (STAT3) were performed to show that interactions between APE1/Ref-1 and the transcription factors it regulates do indeed occur under normoxic conditions with appropriate stimulation (FIGS. 3A & 3B). Interactions of APE1/Ref-1 with HIF1α, and STAT3 were obvious under hypoxic conditions.

Overexpressing APE1/Ref-1 resulted in a stronger signal for both HIF1α and STAT3 immunoprecipitated with APE1/Ref-1 following exposure to hypoxia (FIGS. 2C & 2D). NFκB was still not detected in IPs from cells overexpressing APE1/Ref-1 following exposure to hypoxia indicating that the amount of APE1/Ref-1 was not limiting the above panels (FIGS. 2C & 2D). Another STAT family member, STAT1, was probed to demonstrate that APE1/Ref-1's interactions with the transcription factors are specific to signaling in hypoxia. IPs from Panc10.05 cells were probed for STAT1, which was not detected regardless of the levels of APE1/Ref-1 or oxygen conditions (FIG. 2C). Due to the complexity of the disease and the signaling between various cell types in the pancreatic tumor microenvironment, APE1/Ref-1 interactions with HIF1α, STAT3 and NFκB in CAFs were investigated. The results were identical to the result with PDAC cells: APE1/Ref-1 interacts with HIF1α and STAT3 under hypoxia, but not NFκB (FIGS. 4A-4C) In light of CA9 inhibitors beginning clinical trials and the previous data demonstrating transcriptional regulation of CA9 following APE1/Ref-1 blockade (Fishel et al., Mol Cancer Ther 10(9): 1698-1708), this Example focused on HIF1α signaling and the regulation of the downstream molecule CA9 through APE1/Ref-1.

Figure 5A:
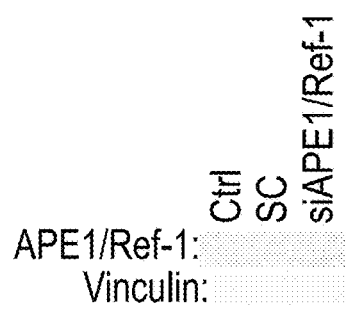
FIGS. 5A-5I show that APE1/Ref-1 protein expression contributes to hypoxia-induced HIF1α-mediated transcription. Particularly, MIA-PaCa2 cells were co-transfected with HIF1α-driven luciferase and Renilla reporter constructs along with scrambled (SC) or APE1/Ref-1-directed siRNA. Knock-down of APE1/Ref-1 was confirmed via western blot (FIG. 5A), and HIF1α-driven luciferase expression was evaluated following 24 hours in hypoxic conditions (0.2% oxygen, vs. normoxia controls) 3-4 days following transfection (FIG. 5B). CA9 mRNA levels were evaluated via qPCR in the cell lines described (FIGS. 5C-5E) using samples collected following transfection with SC or APE1/Ref-1-directed siRNA and 24 hours in hypoxic conditions as shown. APE1/Ref-1 knock-down in MIA-PaCa2 cells with three different siRNAs was confirmed via western blot (FIG. 5F), and CA9 mRNA levels were evaluated via qPCR in SC and knocked-down samples from all three siRNAs following 24 hours in hypoxic conditions (0.2% oxygen, vs. normoxia controls) (FIG. 5G—representative experiment of n=3). CA9 protein levels were evaluated via western blot in 10.05 and CAF19 cells following transfection with SC or APE1/Ref-1-directed siRNA and incubation at 1% oxygen for 24 hours (FIGS. 5H-5I). *$p<0.001$ (Tukey's Multiple Comparisons Test); **$p<0.01$ & #$p<0.001$ (ANCOVA). For CA9 western blots (FIGS. 5H-5I), $p<0.05$ for SC vs. siAPE under hypoxia (Tukey's Multiple Comparisons Test).
Figure 5B:
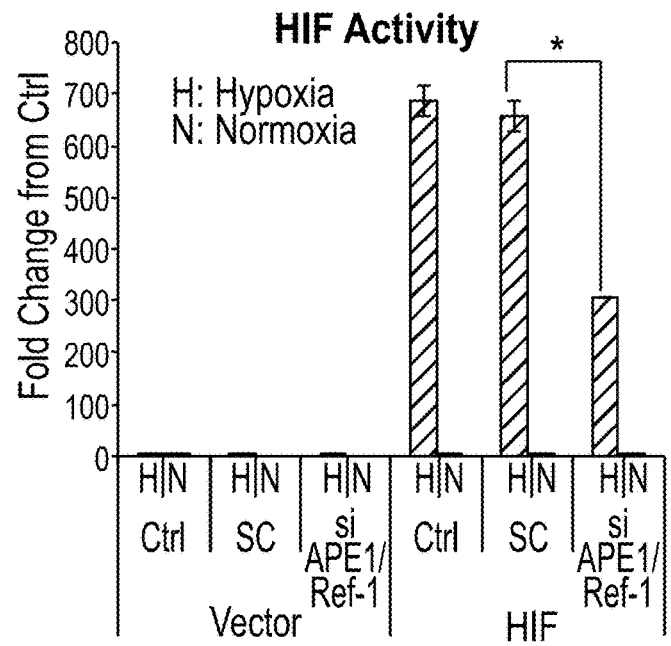

APE1/Ref-1 Protein Expression Contributed to Hypoxia-Induced HIF1α-Mediated Transcription To show that the interactions between APE1/Ref-1 and HIF1α are functionally important, the contribution of APE1/Ref-1 to HIF-1 transcriptional activity was evaluated by co-transfecting MIA PaCa-2 cells with HIF1α-driven firefly luciferase or pLuc-MCS (vector control) alongside APE1/Ref-1 siRNA or scrambled control and exposing cells to hypoxia for 24 hours. APE1/Ref-1 knock-down resulted in a significant reduction (47%) in hypoxia-induced HIF1α activity (FIGS. 5A & 5B).

Figure 5C:
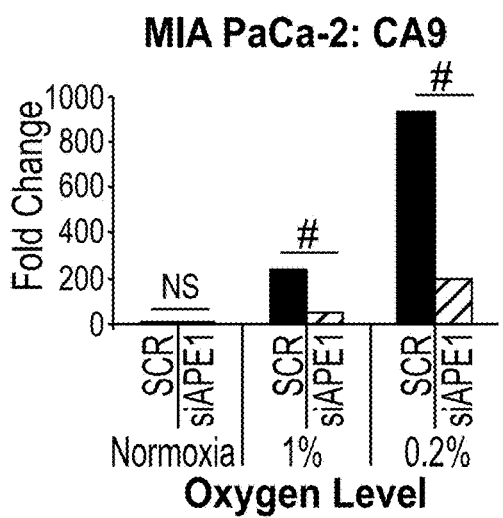
Figure 5D:
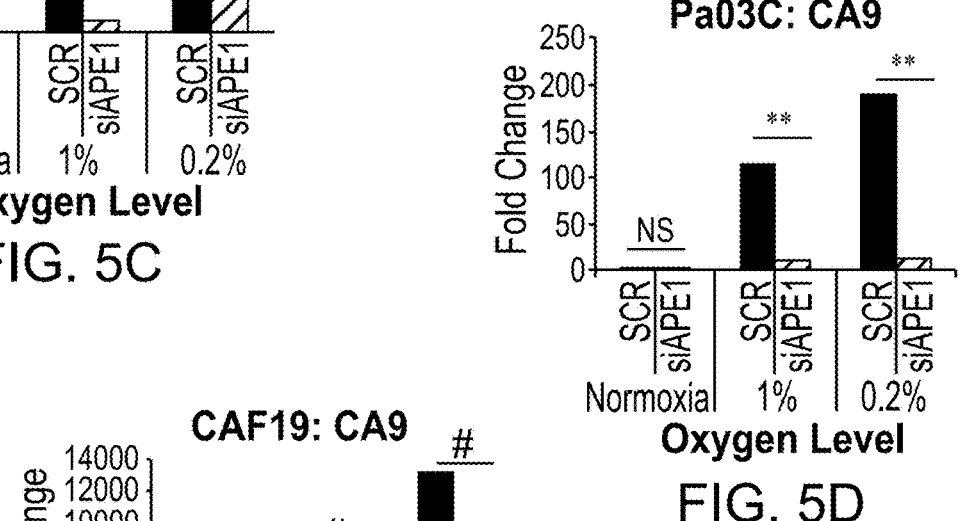
Figure 5E:
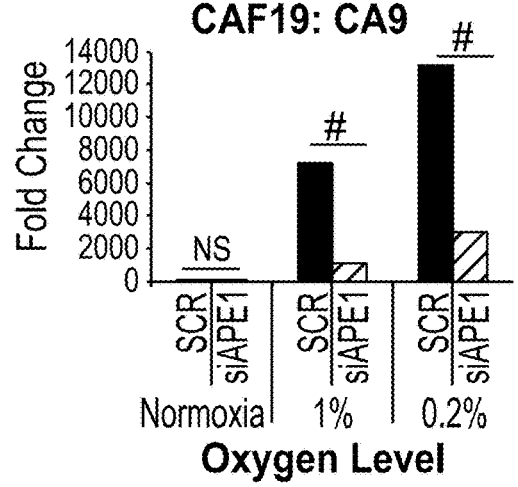
Figure 5F:
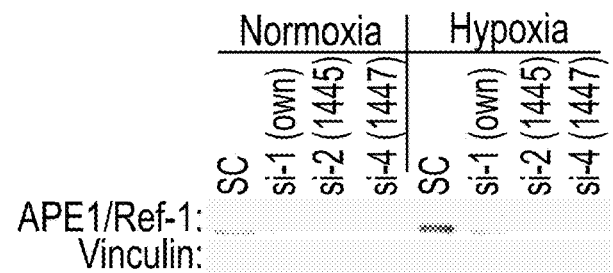
Figure 5G:
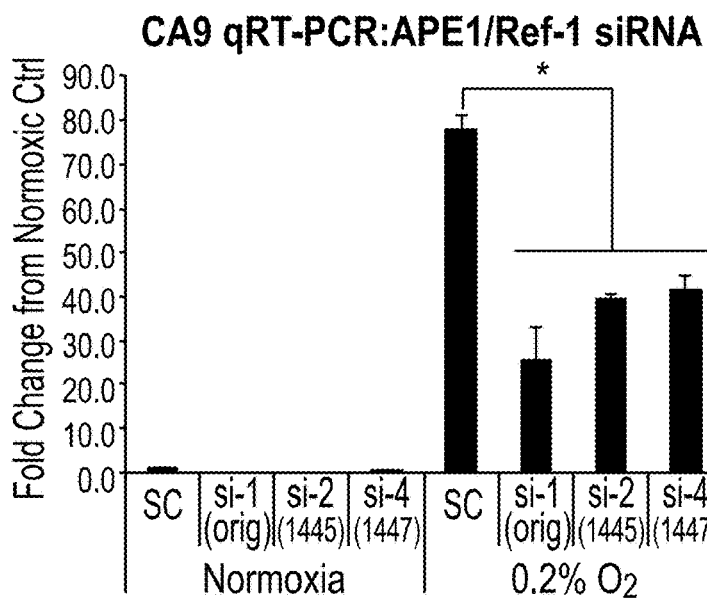
Figure 5H:
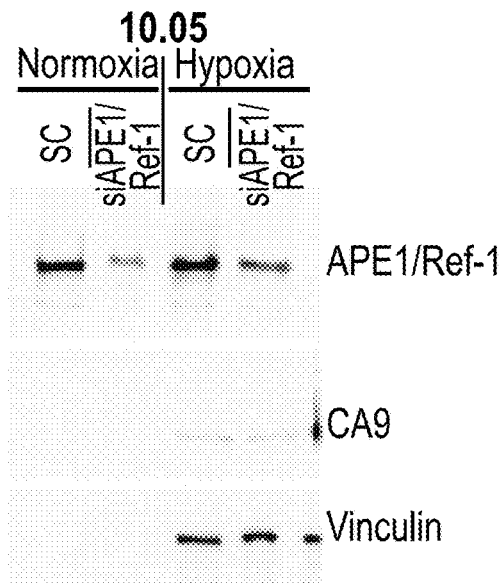
Figure 5I:
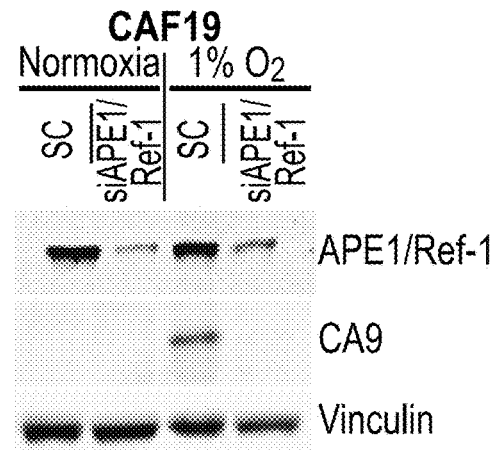
Figure 6A:
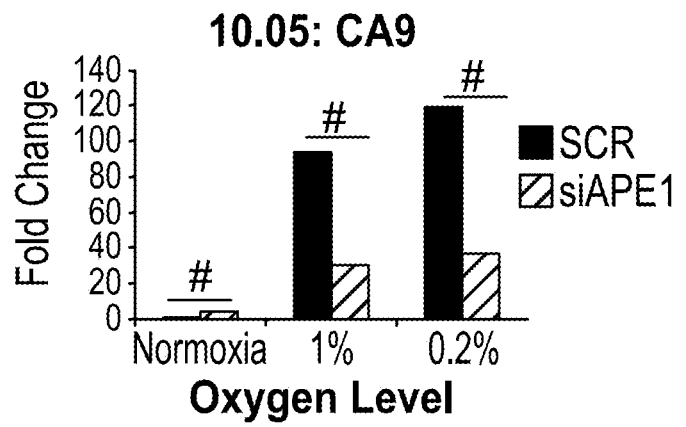
FIGS. 6A & 6B show that APE1/Ref-1 protein expression affects CA9 mRNA levels in additional PDAC cell lines. Particularly, CA9 mRNA levels were evaluated via qPCR in the Panc10.05 (FIG. 6A) and Pa02C (FIG. 6B) cells using samples collected following transfection with SC or APE1/Ref-1-directed siRNA and 24 hours in hypoxic conditions as shown. **$p<0.01$ & #$p<0.001$ (ANCOVA).
Figure 6B:
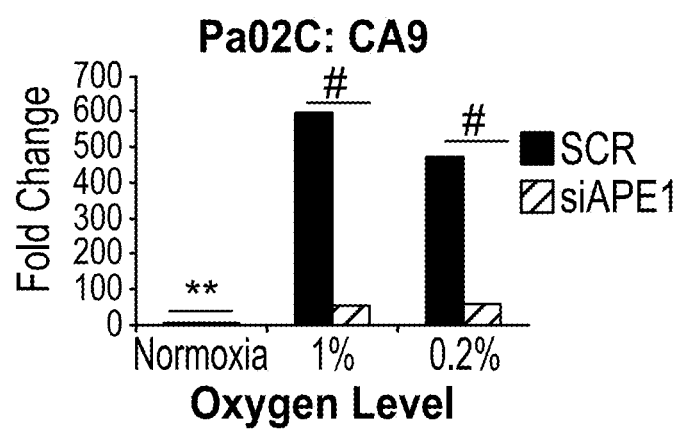

Effects of APE1/Ref-1 on HIF transcriptional activity were further evaluated by examining hypoxia-mediated transcription of the HIF-1 target, CA9. CA9 mRNA levels in two PDAC cell lines and one pancreatic cancer CAF cell line were compared following APE1/Ref-1 knock-down and exposure to hypoxia. Hypoxia-induced CA9 mRNA levels were attenuated by APE1/Ref-1 knock-down in all cell lines at both levels of hypoxia (FIG. 5C-5E). Variability in the amount of induction in different cell lines may be partially attributable to the extremely low baseline CA9 expression under normoxic conditions. APE1/Ref-1 knock-down similarly attenuated CA9 mRNA levels under hypoxid conditions in two additional primary PDAC cell lines (FIGS. 6A & 6B). These results were validated in MIA PaCa-2 cells exposed to hypoxia using two additional APE1/Ref-1-targeting siRNAs, and similar results were obtained (FIGS. 5F-5G). To verify that the reduction in CA9 also occurred at the protein level, hypoxia-induced CA9 protein levels were evaluated via western blot following APE1/Ref-1 knock-down in PDAC cells and pancreatic CAF cells. APE1/Ref-1 knock-down resulted in a ~70% reduction in hypoxia-induced CA9 protein levels (FIGS. 5H-5I).

Hypoxia-Induced CA9 Transcription is HIF-1-Dependent

Figure 7A:
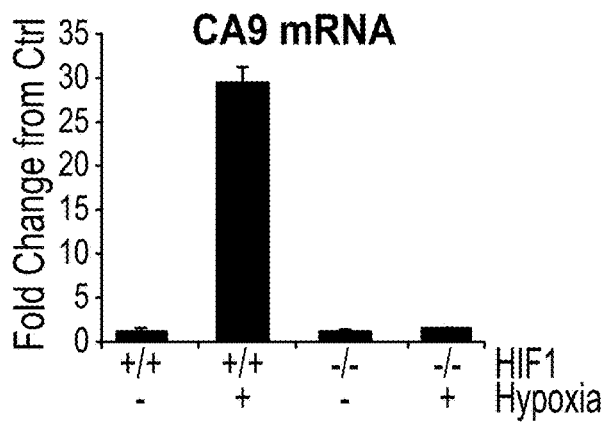
FIGS. 7A-7E show that APE1/Ref-1 redox signaling affects CA9 transcription in a HIF-1-dependent manner Particularly, HIF-1-proficient (+/+) and HIF-1-deficient (−/−) mouse embryonic fibroblasts (MEFs) were exposed to 0.2% oxygen for 24 hours, and CA9 mRNA levels were evaluated by qPCR (FIG. 7A). HIF-1-/- MEFs were transfected with SC or APE1/Ref-1-directed siRNA and incubated at 0.2% oxygen for 24 hours prior to collection and evaluation of CA9 mRNA levels via qPCR (FIG. 7B—representative experiment of n=3). CA9 mRNA levels were evaluated via qPCR in the cell lines described (FIGS. 7C & 7D representative experiments of n=3) using samples collected following 24 hours of exposure to APX3330 and 1% oxygen. Pa03C cells were collected from monolayer (2D) cultures and 3D tumor spheroid cultures grown in the presence or absence of CAFs following treatment with APX3330 as shown, and CA9 protein levels were evaluated via western blot (FIG. 7E). *$p<0.01$ & **$p<0.001$ (Tukey's Multiple Comparisons Test).
Figure 7B:
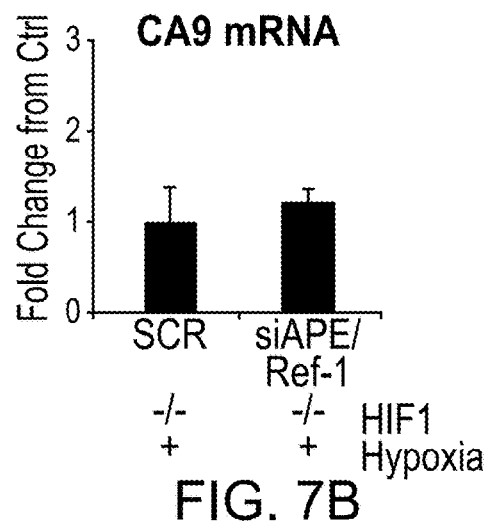

To confirm that the effects of APE1/Ref-1 and hypoxia on CA9 transcription were mediated by HIF-1 activity, hypoxia-induced CA9 mRNA levels were evaluated in HIF-1-deficient (-/-) MEFs following APE1/Ref-1 knock-down. As expected, in HIF-1 proficient MEFs, CA9 was induced 30-fold compared to normal oxygen controls. In HIF-1−/− MEFs, CA9 mRNA levels were not induced by exposure to hypoxia (FIG. 7A), or affected by APE1/Ref-1 knock-down (FIG. 7B), indicating that CA9 transcription is HIF-1-dependent, regardless of APE1/Ref-1 expression or oxygen levels. HIF-1 depletion in these cells was confirmed by PCR (FIG. 1).

Inhibition of APE1/Ref-1 Redox Signaling Affects CA9 Transcription

Figure 7C:
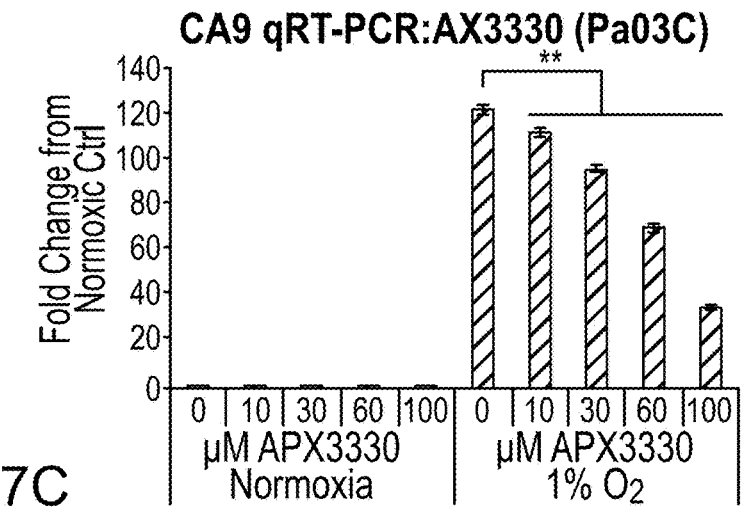
Figure 7D:
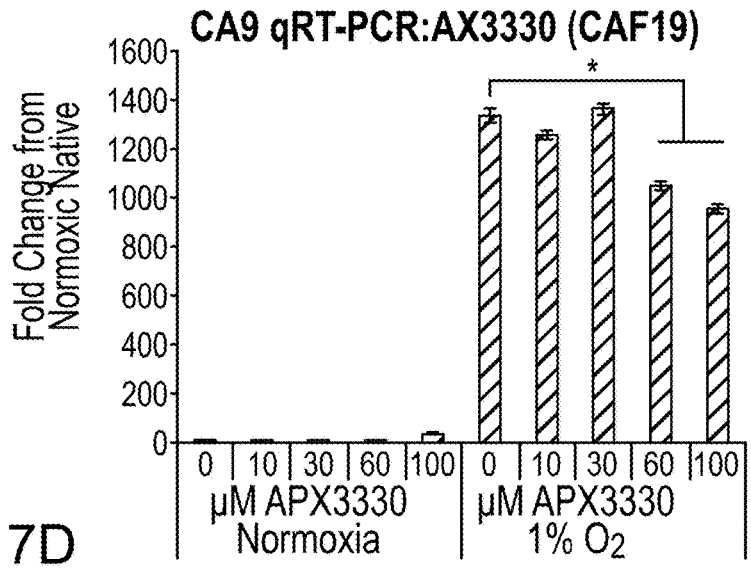
Figure 7E:
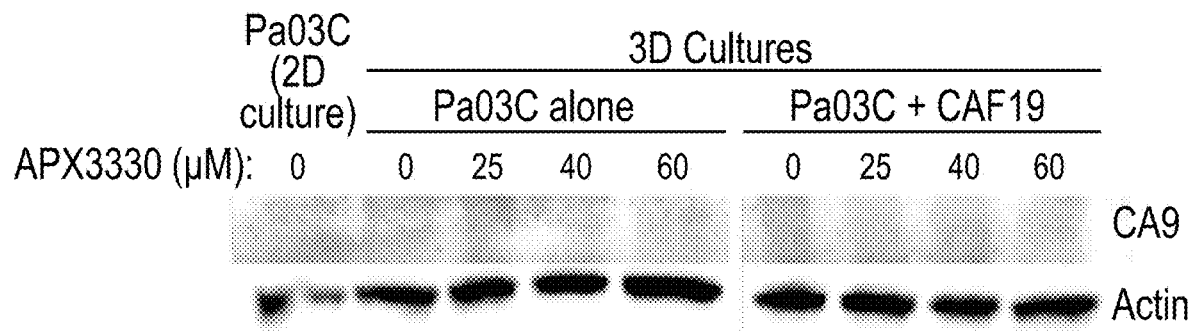

As a multi-functional protein, APE1/Ref-1 is also involved in base excision repair (BER) of DNA lesions, RNA quality control, and reduction-oxidation (redox) regulation. Knock-down of APE1/Ref-1 affects all of these functions. The redox function was examined to determine its responsibility for the APE1/Ref-1-mediated regulation of hypoxia signaling pathways using an APE1/Ref-1 specific redox inhibitor that does not affect other APE1/Ref-1 functions and is slated for clinical trial in the summer of 2016. It was previously shown that APX3330 decreases CA9 mRNA levels in Panc-1 and MIA-PaCa2 cells exposed to hypoxia. Here these results are expanded to primary cells and CAF cells, as well as 3D co-cultures. Following treatment with APX3330 and exposure to hypoxia, CA9 mRNA levels in Pa03C cells and in pancreatic CAF cells were attenuated in a dose-dependent manner (FIGS. 7C & 7D). Additionally, CA9 protein expression was measured in a 3D co-culture model following inhibition of APE1/Ref-1 with APX3330. While CA9 was not detected under normoxic conditions in the patient-derived Pa03C cells in monolayer, when grown as spheroids, these cells expressed CA9. Tumor spheroids grown in the presence of CAFs more strongly upregulated CA9 expression (~3-fold), likely due to larger spheroids containing larger regions of hypoxia, as well as the more complex signaling present with the stromal elements. Inhibition of APE1/Ref-1 redox signaling with APX3330 led to decreased CA9 expression in 3D tumor cultures in a dose-dependent manner, both in the presence and absence of CAF cells (FIG. 7E). These data support the use of the 3D co-culture system for preclinical studies validating novel targets like CA9 and APE1/Ref-1 in PDAC.

Figure 8A:
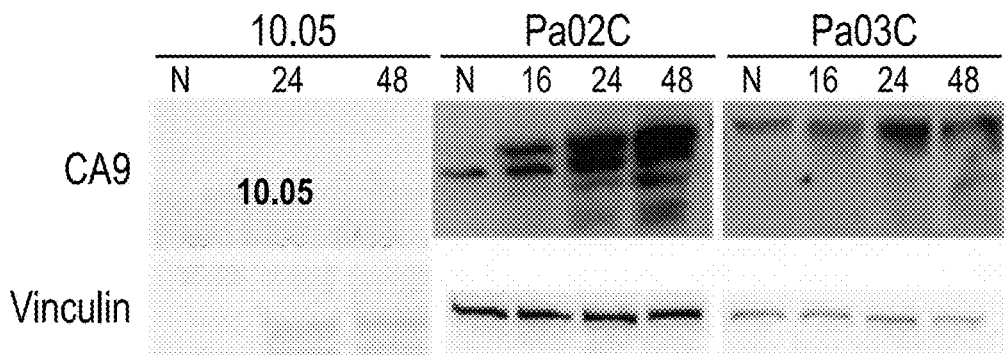
FIGS. 8A & 8B show that CA9 protein levels are increased under hypoxia, but APE1 levels are not. Particularly, PDAC cells were exposed to 0.2% oxygen for the times indicated, and CA9 and APE1/Ref-1 protein levels were evaluated via western blot.
Figure 8B:
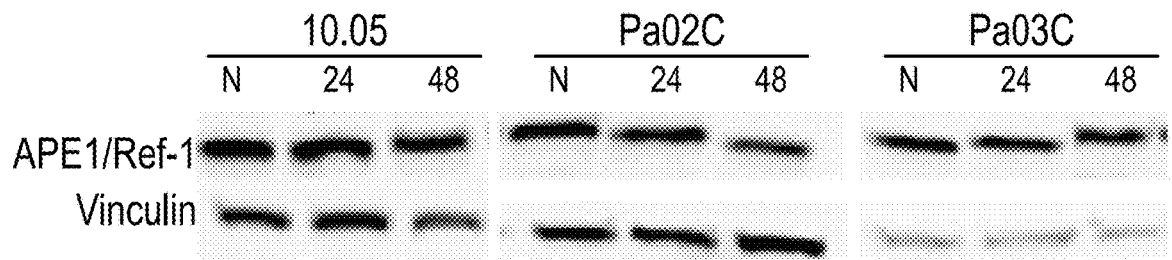

CA9 and APE1/Ref-1 protein expression was evaluated following exposure to hypoxia (0.2% oxygen) in three PDAC cell lines and found that, while CA9 levels increased over time, APE1/Ref-1 levels did not change significantly (FIGS. 8A & 8B), indicating that hypoxia-induced CA9 expression is not secondary to APE1/Ref-1 upregulation.

Figure 9A:
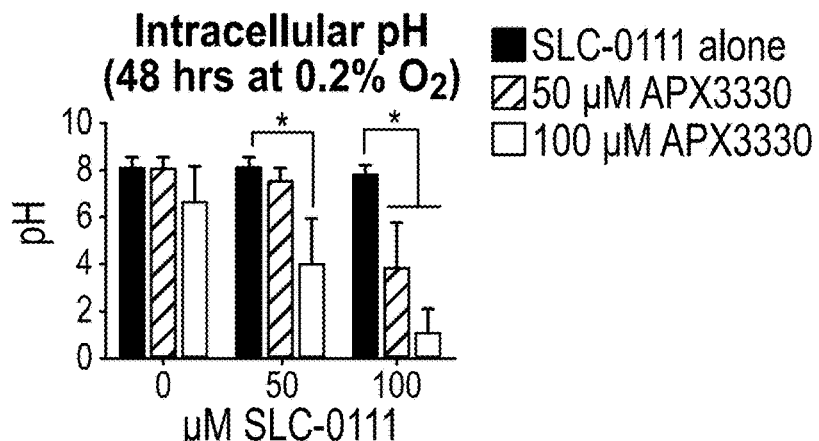
FIGS. 9A-9C show that dual-targeting of CA9 and APE1/Ref-1 acidifies PDAC cells and inhibits cell proliferation under hypoxia. Panc10.05 cells were treated with the indicated concentrations of APX3330 and SLC-0111 and exposed to hypoxia (0.2% $O_2$) for 48 hours prior to analysis of intracellular pH (FIG. 9A). Pa02C cells were treated with the indicated concentrations of APX3330 and SLC-0111 (FIG. 9B) or FC13-555A (FIG. 9C) and exposed to hypoxia (0.2%) for six days. *$p>0.05$ & **$p<0.01$ (Dunnett's Multiple Comparisons Test); #$p>0.05$ & ##$p<0.01$ (Sidak's Multiple Comparisons Test). Differences in nonlinear regression curves between treatment groups were confirmed using extra-sum-of-squares F tests followed by Bonferroni Corrections in each experiment ($p<0.05$ for all dual-treatment curves vs. single-agent curves).

Dual-Targeting of CA9 and APE1/Ref-1 Acidifies PDAC Cells and Inhibits Cell Proliferation Under Hypoxia CA9 regulates intracellular pH under hypoxic conditions, and APE1/Ref-1 redox activity contributes to hypoxia-induced CA9 expression. Intracelllular pH was analyzed in hypoxia-exposed PDAC cells following treatment with the CA9 inhibitor, SLC-0111, and the APE1/Ref-1 redox inhibitor, APX3330 using the pHrodo Red AM fluorescent pH indicator as a functional endpoint for carbonic anhydrase activity under hypoxic conditions. Dual treatment with SLC-0111 and APX3330 resulted in a greater decrease in intracellular pH as compared to treatment with either inhibitor alone (FIG. 9A).

Figure 9B:
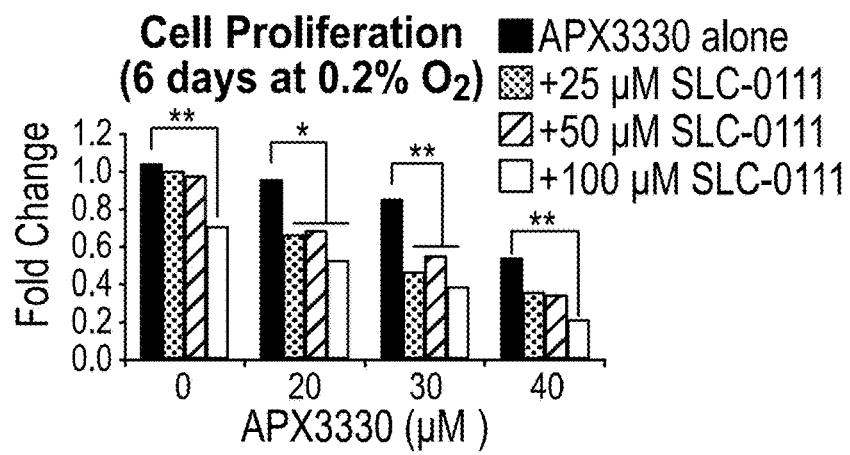
Figure 9C:
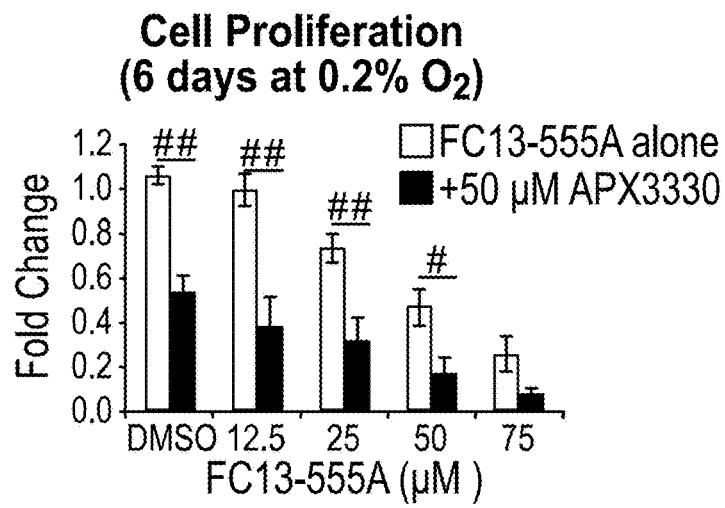

Inhibition of APE1/Ref-1 redox activity resulted in a dose-dependent decrease in PDAC cell proliferation following treatment of cells with APX3330 and hypoxia. The effect of APE1/Ref-1 inhibition on cell viability was greatly enhanced by treating with the CA9 inhibitor, SLC-0111, in addition to APX3330 treatment under hypoxia (FIG. 9B). Further, the combination of APX3330 with the SLC-0111 analog, FC13-555A, was also found to be significantly effective at killing PDAC cells in a monolayer (FIG. 9C), supporting the hypothesis that blockade of hypoxia signaling proteins will be deleterious to PDAC cells. In support of these results, new CA9 inhibitors are being developed.

Figure 10A:
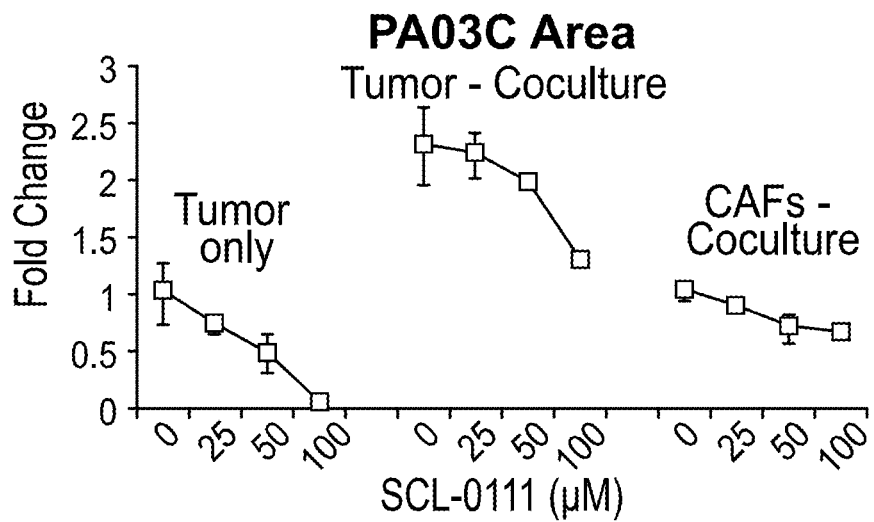
FIGS. 10A-10F show that dual-targeting of CA9 and APE1/Ref-1 inhibits PDAC tumor growth in a 3D co-culture model. Particularly, Pa03C (FIGS. 10A, 10C, & 10E) and Panc10.05 (10B, 10D, & 10F) tumor cells (transduced with TdTomato) were grown in 3D cultures in the presence and absence of CAFs (transduced with EGFP). Spheroids were treated with SLC-0111 alone (FIGS. 10A & 10B) and in combination with APX3330 (FIGS. 10C & 10D), and the area of tumor and CAF were quantified following 12 days in culture. Representative images from dual-treatment experiments are shown in FIGS. 10E and 10F. Differences in nonlinear regression curves between treatment groups were confirmed using extra-sum-of-squares F tests followed by Bonferroni Corrections in dual-treatment experiments ($p<0.01$ for each curve vs. the curve for APX3330 alone in tumor cells alone, $p<0.01$ for curves with 50 μM SLC-0111 vs. the curve for APX3330 alone in tumor+CAF co-cultures).
Figure 10B:
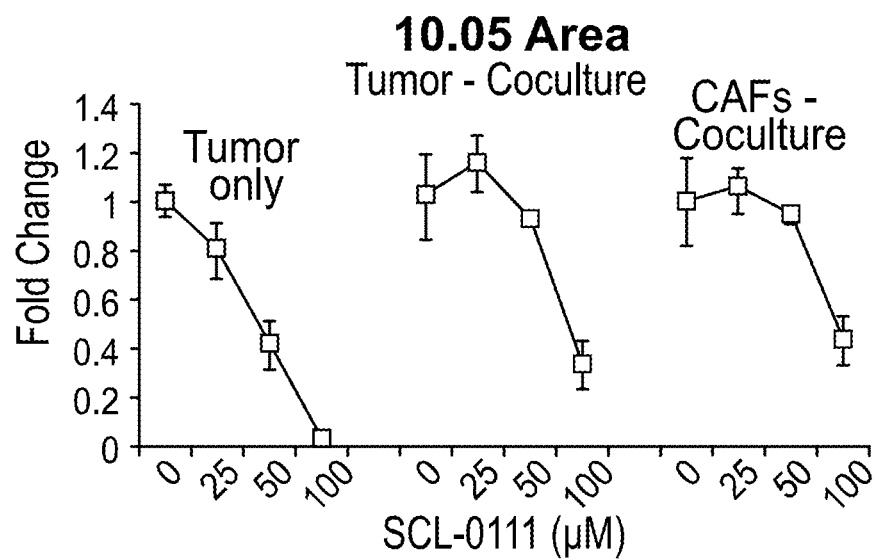

Dual-Targeting of CA9 and APE1/Ref-1 Inhibited PDAC Tumor Growth in a 3D Co-Culture Model In order to more accurately mimic the tumor microenvironment, a three-dimensional co-culture model of PDAC was utilized that included the low passage patient derived tumor cells as well as cancer-associated fibroblasts. As demonstrated above, the levels of CA9 were greater in these tumor spheroids when grown with CAF cells, and CA9 expression was attenuated by treatment with APX3330 (FIG. 7E). Inhibition of CA9 with SLC-0111 was more potent in the 3D model with dramatic effects on tumor cell killing observed at lower doses than in a monolayer, as measured by reductions in area of patient-derived cells (FIGS. 10A & 10B). Cell killing was more dramatic in the tumor cells than in the CAFs, especially when CAF19 cells were in co-culture with Pa03C cells. Similar trends were seen when measuring fluorescence intensity (data not shown). Importantly, inhibition of CA9 can effectively kill tumor cells even when in the protective environment of the CAFs.

Figure 10C:
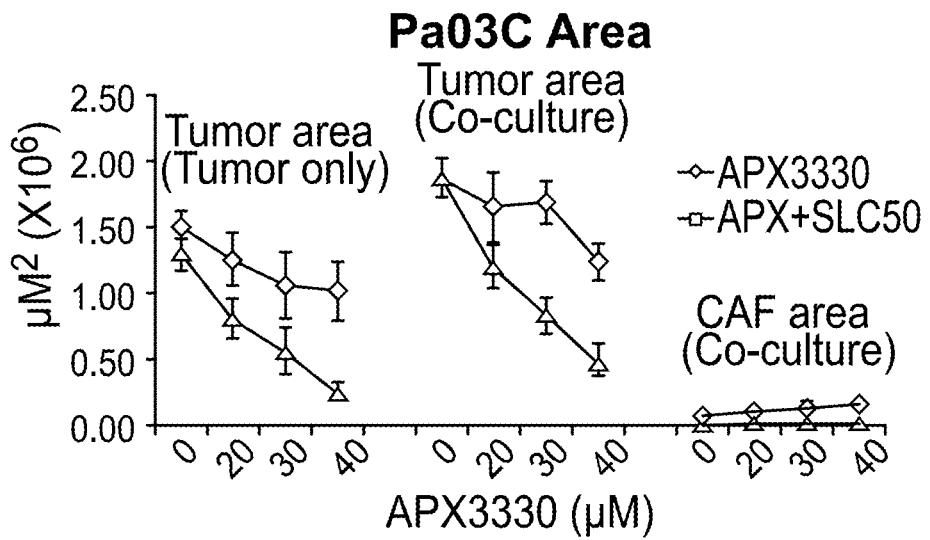
Figure 10D:
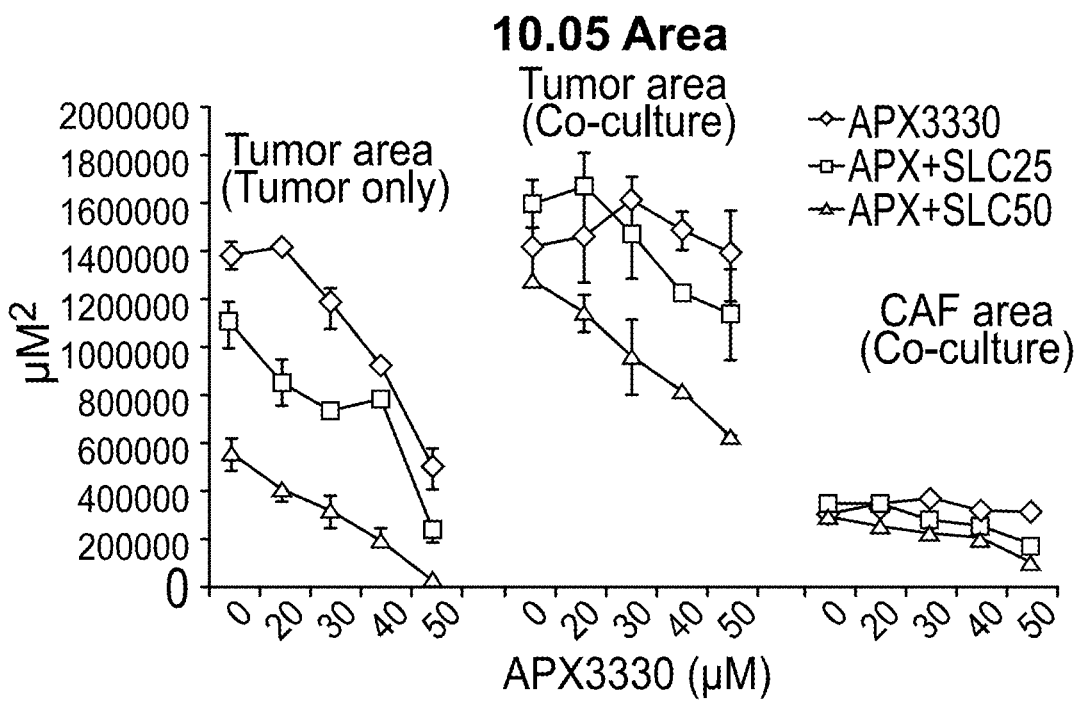
Figure 10E:
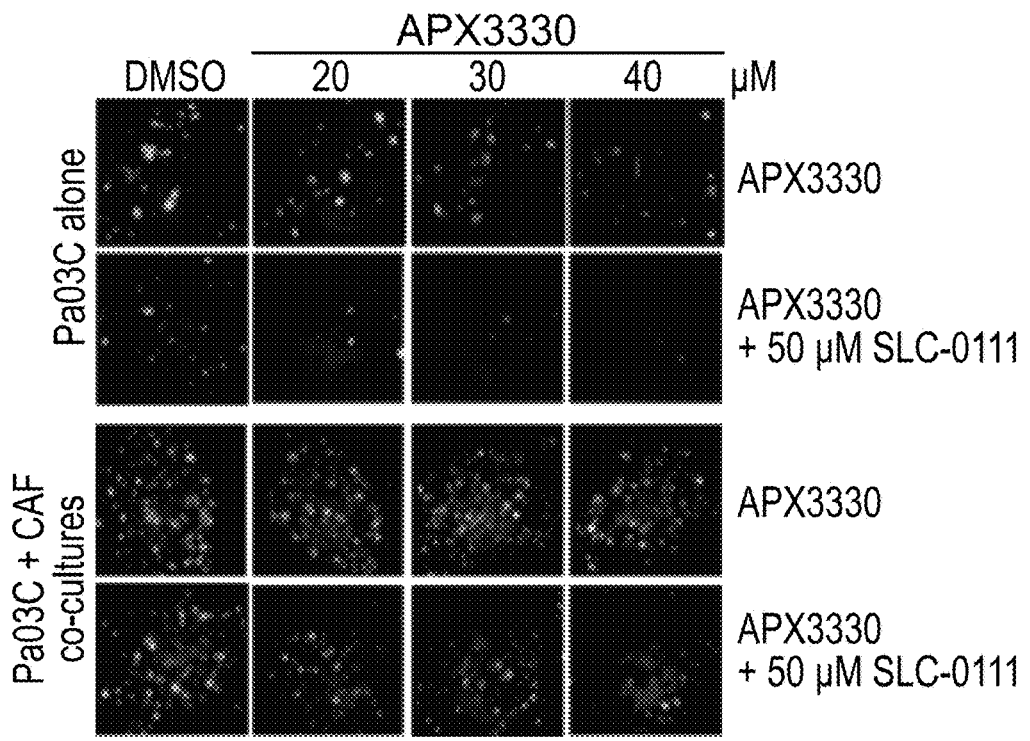
Figure 10F:
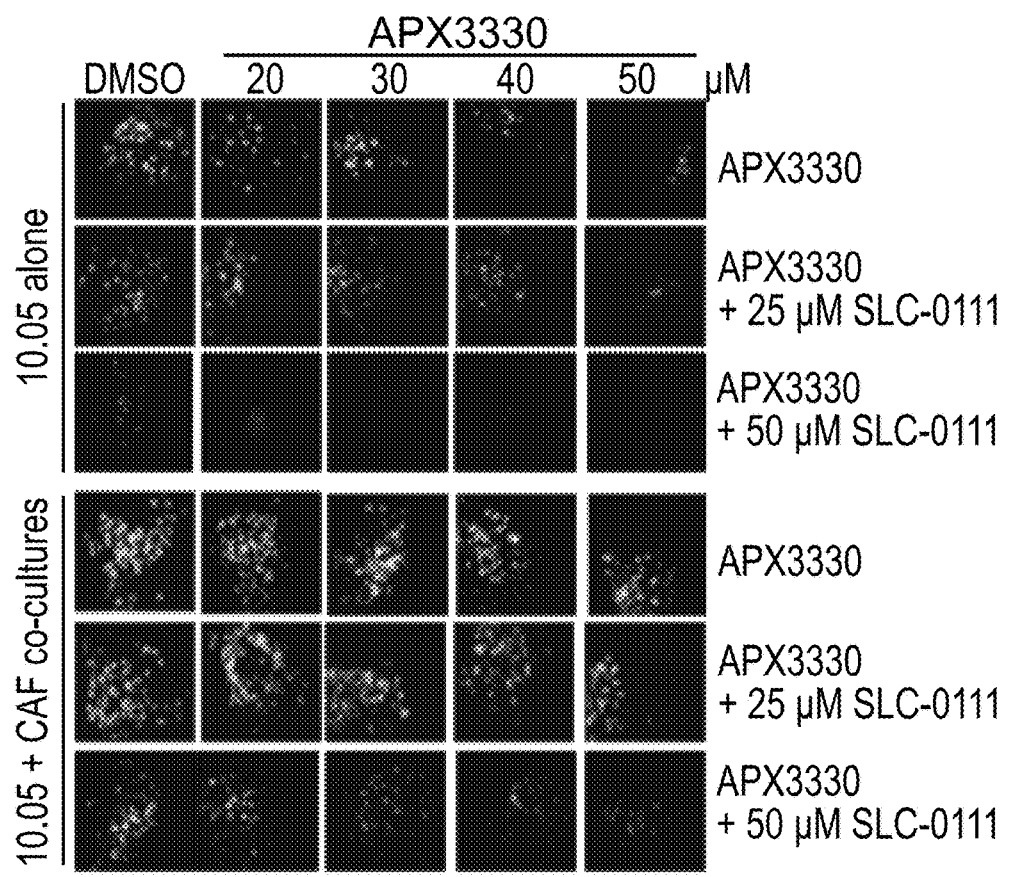

To determine if blockade of STATS and HIF-mediated transcription alongside the inhibition of CA9 activity would potentiate PDAC cell death, APX3330 and SLC-0111 was combined in the 3D co-culture model. The effects of dual targeting on both the tumor alone and the tumor and CAFs in co-culture could be assessed due to the different fluorescent labels in each cell type. As seen in hypoxia-exposed 2D cultures, addition of CA9 inhibition to APE1/Ref-1 redox inhibition resulted in dramatic potentiation of the cell killing in the tumor spheroids. Spheroids composed of patient-derived PDAC cells (Pa03C or Panc10.05) and CAF cells were treated with APX3330 and SLC-0111 (FIGS. 10E & 10F), and the area of fluorescence were evaluated separately as markers for each cell type (FIGS. 10C & 10D). Dramatic enhancement of the APX3330-induced blockade of spheroid growth was observed with the addition of CA9 inhibition. The observed decrease in tumor cell area with APX3330 treatment was significantly different in the presence of SLC-0111, validating the effects seen in hypoxia-exposed 2D cultures. Similar trends were seen when measuring red and green fluorescence intensity (data not shown).

Discussion

Figure 11A:
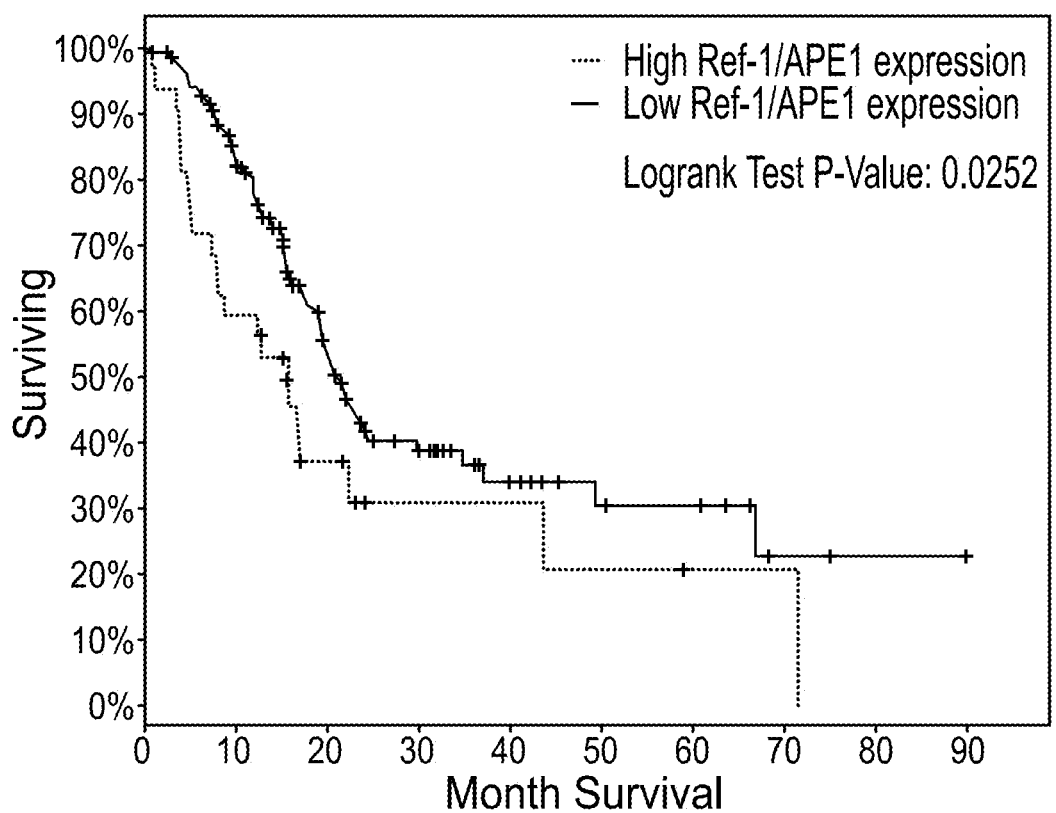
FIGS. 11A-11D show that APE1 expression correlates with decreased survival in PDAC, and CA9 is upregulated in PDAC. Comparison of overall survival in PDAC patients with low vs. high expression of APE1/Ref-1 mRNA was obtained from The Cancer Genome Atlas (TCGA) database (FIG. 11A). Comparison of CA9 mRNA levels in normal pancreas vs. PDAC (FIGS. 11B & 11D) or pancreatic cancer precursor vs. PDAC (FIG. 11C) was obtained from Oncomine using data provided by Logsdon et al.
Figure 11B:
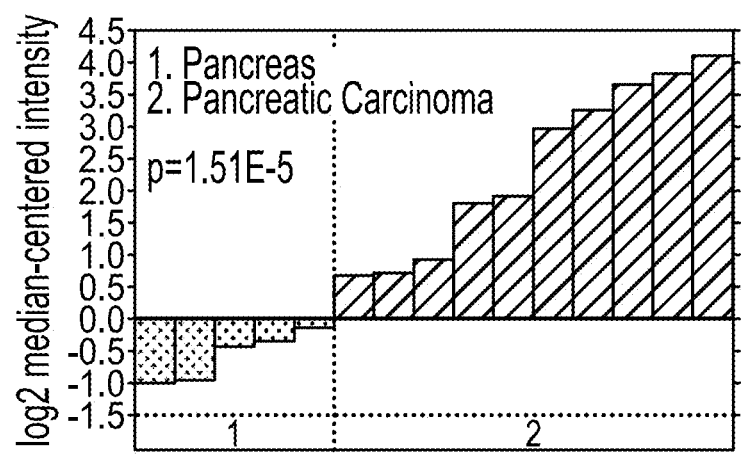
Figure 11C:
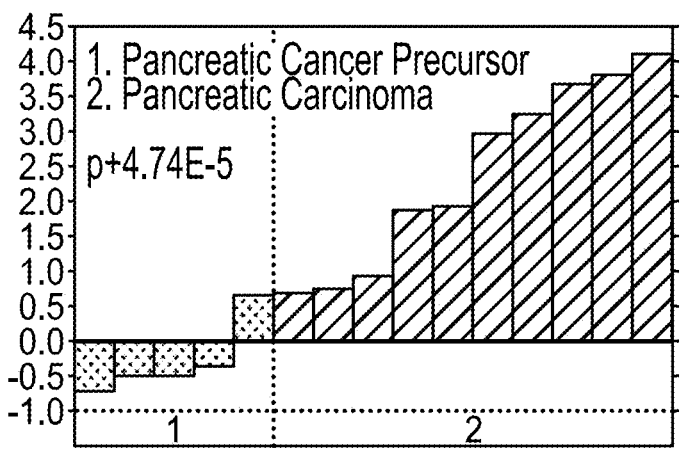
Figure 11D:
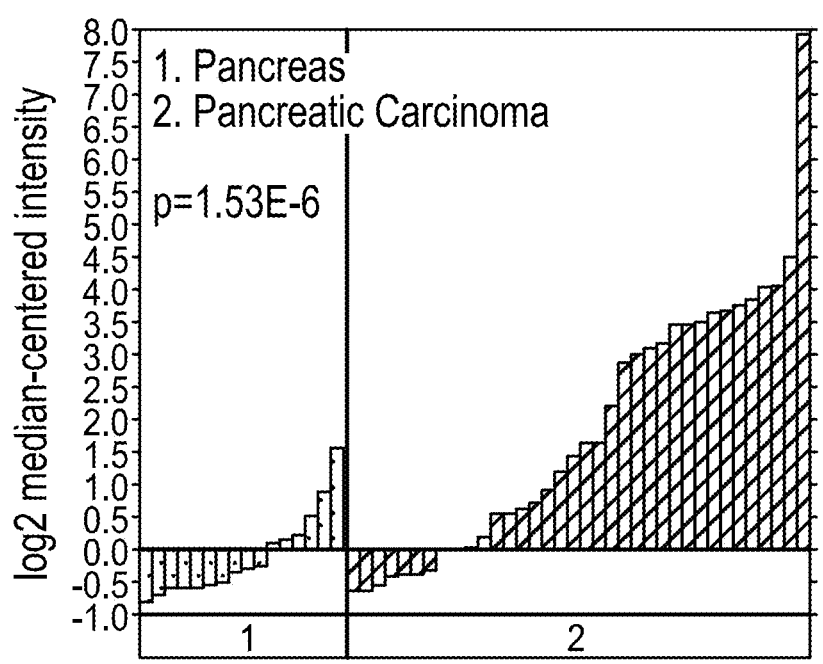

Elevated APE1/Ref-1 expression is associated with numerous cancers, including pancreatic, ovarian, gastric, breast, lung, glioblastoma, liver, and colon, and analysis of publicly available data from The Cancer Genome Atlas (TCGA, cancergenome.nih.gov) reveals a significant decrease in survival of PDAC patients with elevated APE1/Ref-1 expression (FIG. 11A). In tumor cells, reduction-oxidation (redox) of thiols of cysteines in various tumor-promoting transcription factors (TFs) such as STAT3, NFκB, and HIF-1 by APE1/Ref-1 is a crucial step in the activation of these factors. These TFs are all important targets in cancer therapy and particularly PDAC, but have been shown to be particularly hard to drug.

APE1/Ref-1 contributes to STAT3 activation and the consequent tumor-promoting effects of STAT3 in PDAC cells. The cooperative activities of STAT3 and HIF-1 have been demonstrated in a variety of cancers; however, the finding in the present disclosure that APE1/Ref-1 binding to STAT3 is stimulated by exposure to hypoxia in PDAC cells indicates the importance of both APE1/Ref-1 and STAT3 as potential therapeutic targets in PDAC. These findings will be further pursued with preclinical STAT3 inhibitors that are being developed for eventual clinical trials. Furthermore, the above results, demonstrating that APX3330 treatment decreases hypoxia-induced HIF-1 transcriptional activity and CA9 mRNA levels, is exciting since CA9 inhibitors are either entering or are in clinical trials. This latter finding is of great interest, not only because it is closer to patient applicability, but builds upon a strategy of blocking various signaling pathways at multiple points along pathways influenced by APE1/Ref-1.

The strategy of the present disclosure of inhibiting the HIF-CA9 axis at two points; blocking HIF-1 production of CA9 with APX3330 as well as blocking the activity of any CA9 that is produced using SLC-0111, is a novel approach to the targeting of hypoxic PDAC cells. That being said, not only hypoxic PDAC cells will be sensitive to the combination of APX3330 and SLC-0111. APX3330 is targeting other signaling pathways that are activated in tumor cells that are fully oxygenated, and SLC-0111 can also inhibit CA12, another tumor-associated carbonic anhydrase. The above findings establish this strategy resulting in additive cell acidification and inhibition of hypoxic PDAC cell proliferation.

In conclusion, the Example presented here provides continued evidence of the close relationship between APE1/Ref-1, STAT3, and HIF-1 signaling and CA9 production in PDAC as well as the first evidence that the combination of two small molecule inhibitors, each showing minimal toxicity, may be an important next step in the treatment of PDAC, a disease for which effective treatment remains elusive.

Example 2

In this Example, the dual targeting effects of Ref-1/STAT3 on cell survival and proliferation were analyzed.
Materials and Methods
Three-Dimensional Growth Assays.

Ninety-six well plates were coated with 1% Noble Agar (Difco) (50 µL/well). mCherry-labeled PDAC cells and EGFP-labeled CAFs were resuspended in normal growth media containing 3% Matrigel (BD Biosciences) at a cell ratio of 1:4 (tumor:CAF) and plated on top of solidified 1% Noble Agar. Cells were fed on Days 4 and 8 following plating with media containing 5% serum+3% Matrigel+ investigational drug.

Utilizing APX3330, JAK 2 inhibitor (Ruxolitinib (INCB018424; Fisher Scientific) ("RUX")) and lead STATS inhibitors (PG-S3-001, DR-4-89), the effects of Ref-1/STAT3 inhibition in PDAC low passage patient-derived cell lines (Pa03C and Panc10.05) were evaluated. The response using proliferation-based 3D co-culture assays and statistical analyses to assess synergy, additively or antagonism was evaluated using the Chou-Talalay method.

Figure 12A:
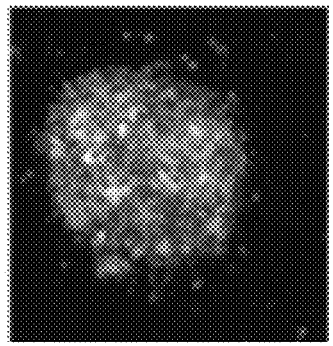
FIGS. 12A & 12B are confocal images of co-culture tumor spheroids with PG-S3-001 (FIG. 12B) and without (FIG. 12A) STAT5 inhibition.
Figure 12B:
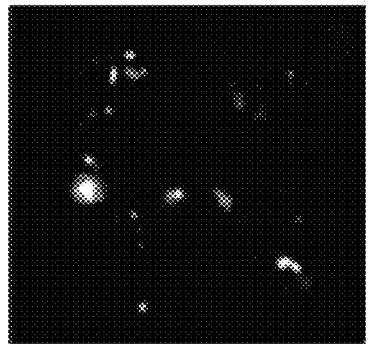
Figure 13:
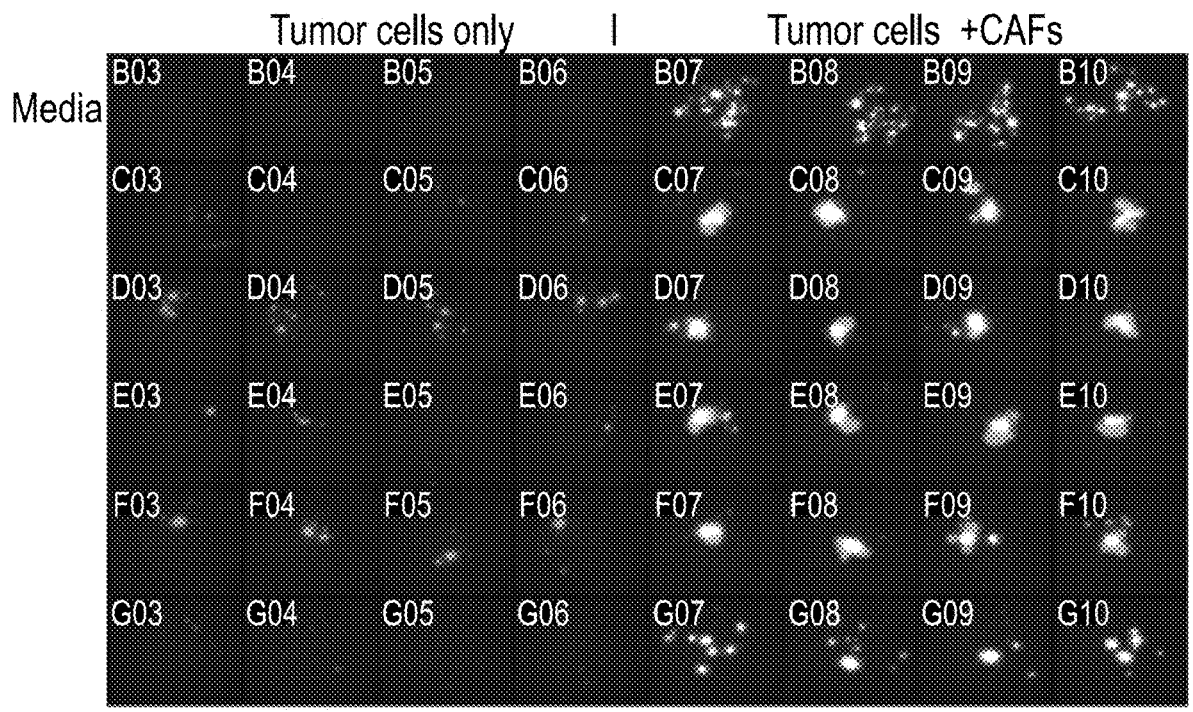
FIG. 13 depicts 3D cell plating using Thermo ArrayScan where two-dimensional projections of 3D structures were processed to quantify differences in total intensity and total area of each cell population. Day 10: Tumor=Pa03C Red, CAFs=CAF19 Green. Lower line shows tumor killing wherein red (tumor) is gone and green (CAF) remains. Yellow on right side of panel is result of red (tumor) and green (CAF) overlap. All colors not shown in FIG. as filed.
Figure 14:
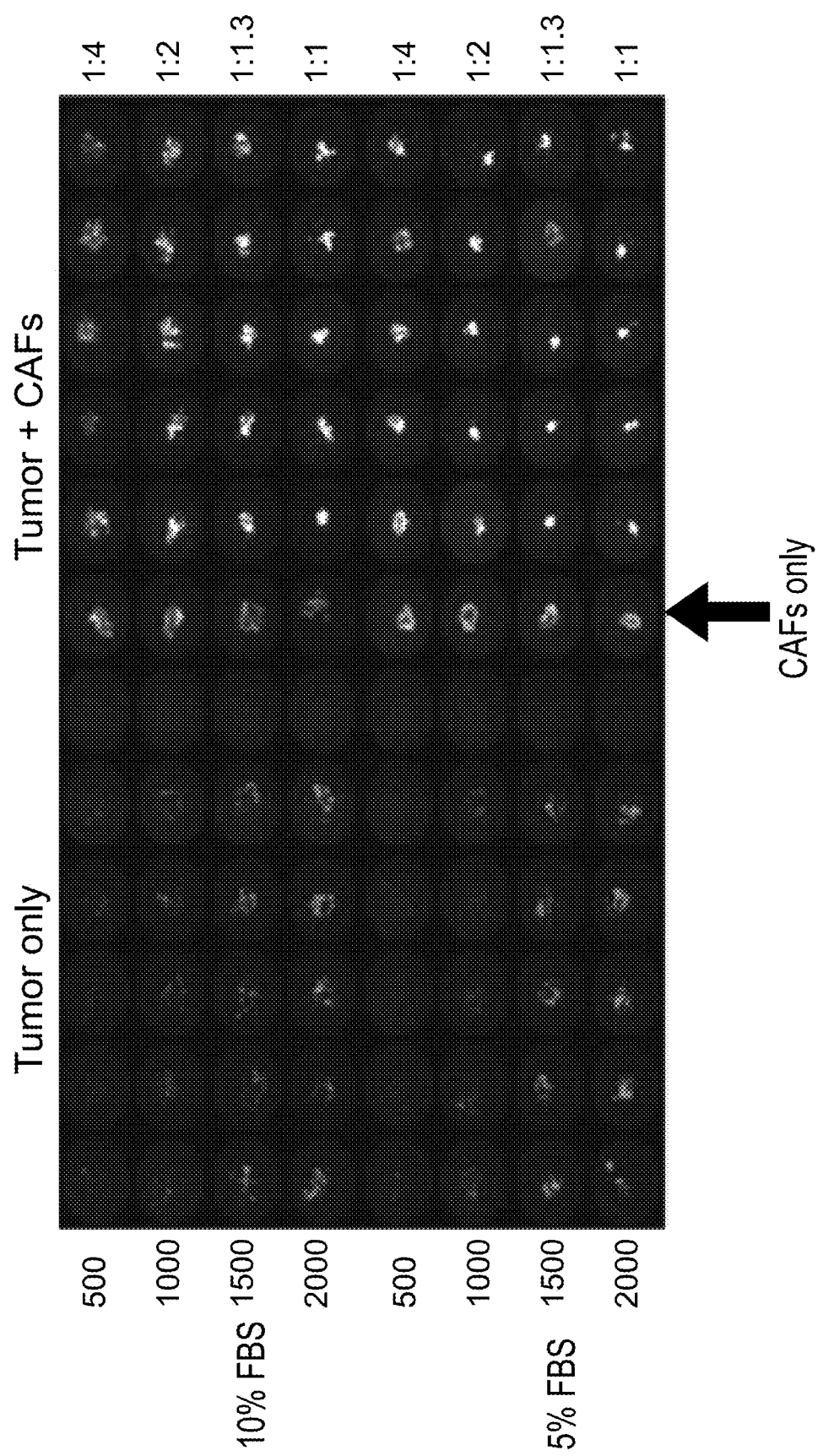
FIG. 14 depicts drug efficacy of PDAC cells evaluated in co-culture with CAFs.

This Example was designed to visualize the same live co-cultures over 12 days with images captured by Thermo ArrayScan at 8 and 12 days of co-culture. Cancer and stromal cells in this model were marked with distinct fluorescent proteins (mCherry for tumor and EGFP for CAFs) so that the cell populations could be differentiated and quantified. Several factors enabling usage of 3D co-cultures were previously optimized to screen for effective combinations, including the appropriate plate for 3D culture and imaging (96-well plate), number of tumor cells (1000 cells) needed per well to form stable structures, and the ratio of tumor to CAFs that is optimal (1:4) (FIGS. 12A & 12B). A semi-high-throughput system was developed using Thermo ArrayScan where two-dimensional projections of 3D structures could be readily processed to quantify differences in total intensity and total area of each cell population (FIG. 13). In this way, drug efficacy of PDAC cells could be evaluated in co-culture with CAFs, which more faithfully mimics the natural in vivo PDAC environment.
Results Single agents, APX3330, RUX, PG-S3-001, and DR-4-89 have already been tested in the 3D assay. These agents effectively killed both tumor spheroids alone and in culture with CAFs. Particularly, inhibition of STAT3 with lead compounds, PG-S3-001 and DR-4-89, resulted in cell death in PDAC cells, even in the presence of CAFs, and as a single agent, some activity was observed in vivo (FIG. 14).

This model was used to test combinations of APX3330 and STAT3 inhibition. Because of the semi-high throughput nature of the system developed using the ArrayScan and 96-well plate format, a large number of combinations and doses of each drug can be conducted. Using both PG-S3-001 and DR-4-89 as well as STAT3 pathway with RUX will help to ascertain whether direct STAT3 inhibition is more potent than upstream inhibition of STAT3 through JAK2.

Figure 15:
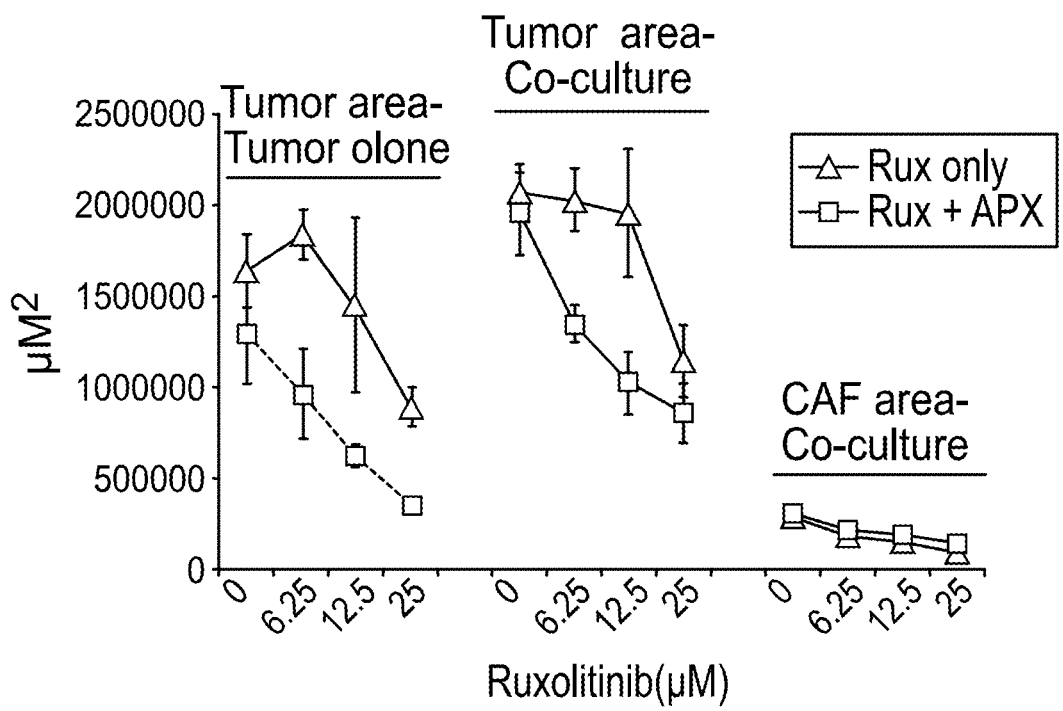
FIG. 15 depicts effects of the combination of RUX with APX3330 on tumor killing.

As shown in FIG. 15, RUX in combination with APX3330 effectively killed both tumor spheroids alone and in culture with CAFs.

Example 3

In this Example, the in vivo effect of a combination of APX3330 and Ruxolitinib (RUX) on PDAC survival was analyzed.

Figure 16:
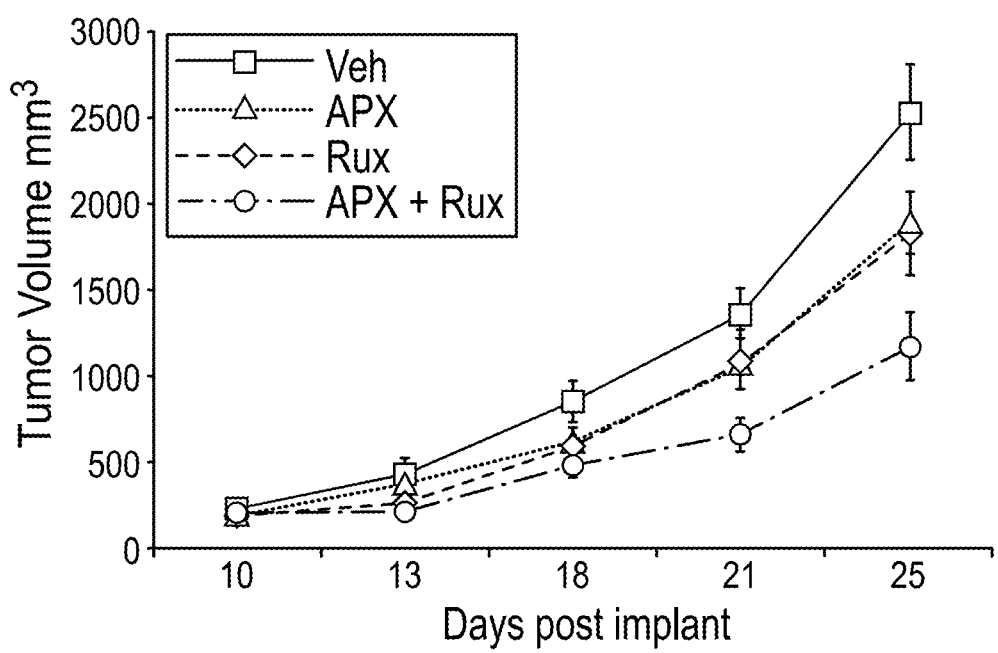
FIG. 16 depicts the dual targeting effects of the combination of RUX with APX3330 on PDAC survival.

Utilizing APX3330 and RUX, the effects of Ref-1/STAT3 inhibition in an in vivo co-culture model with low passage patient-derived cell lines (Pa03C) co-injected with CAFs were evaluated. Particularly, NSG mice (n=5 per treatment group) were treated with 50 mg/kg APX3330 BID IP for 5 days on, 2 days rest for 2 weeks and/or RUX given IP SID at 50 mg/kg at each afternoon treatment. As shown in FIG. 16, the co-treatment of APX3330+RUX potently inhibited tumor growth in this co-culture in vivo model. Sub-lethal doses of the single agents (50 mg/kg) were used in order to see the effect of the combination treatment, and the combination treatment was well tolerated in the mice.

Based on the foregoing, dual targeting of these two proteins represents a synthetic lethal event for PDAC cells.

Example 4

Figure 17:
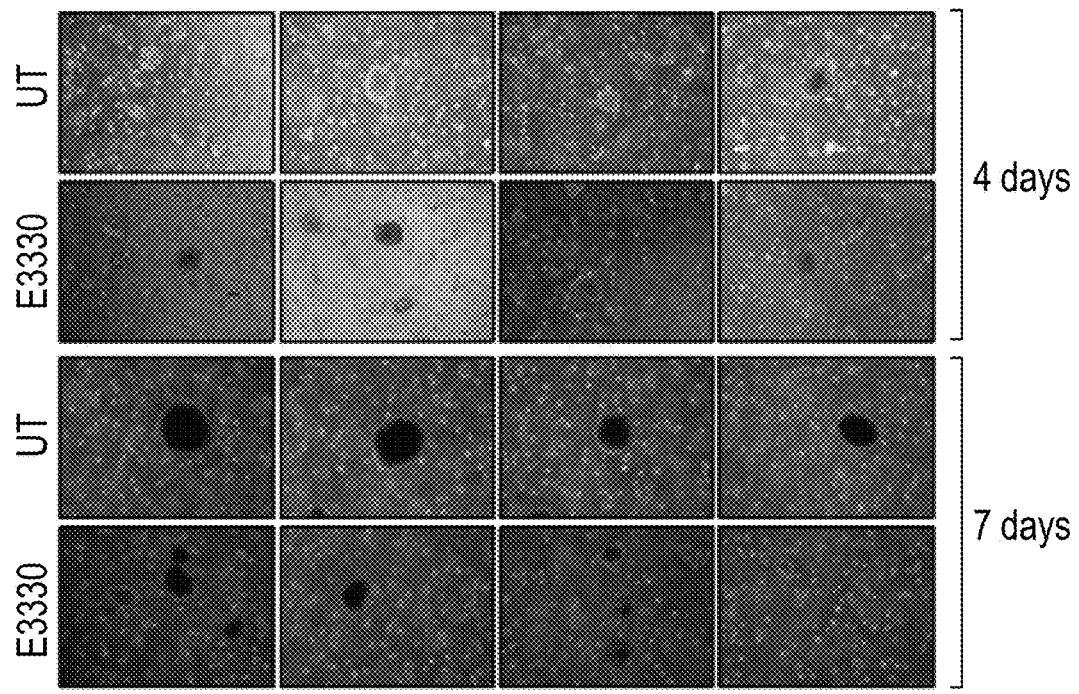
FIG. 17 depicts the effects of E3330 on tumor formation in the ST8814 MPNST cell line. Tumor growth was monitored over 4 and 7 days. Objective 10×.

In this Example, the effects of Ref-1 inhibition on cell survival and proliferation in malignant peripheral nerve sheath tumors (MPNST) cell lines were analyzed.
Methods and Materials ST8814 MPNST cells, derived form a NF1 patient, were purchased from ATCC (distributed by LGC Standards, Middlesex, UK). The 5462 MPNST cell line, a cell line established from MPNST 24472, was taken from a 19-year old female NF1 patient. All cell lines mentioned were cultured in 75 cm$^2$ flasks with Dulbecco's Modified Eagle's Medium (DMEM) supplemented with 10% (v/v) Foetal Calf Serum (FCS) and 1% (v/v) Pen Strep. Cell lines were incubated at 37° C. in 5% $CO_2$.
Soft Agar Tumor Formation Assays Two-layered soft agar assays were undertaken in six-well plates. Briefly, 10$^3$ MPNST cells were plated in complete media containing 0.35% agar over a 0.6% agar layer. Agar was overlaid with complete media and cell colonies were grown for 7 days at 37° C. in 5% $CO_2$. Media was changed three times a week, and plates were treated with 50 μM of E3330 every time media was changed. Representative phase contrast pictures were taken using an inverted AMG EVOS microscope equipped with an Olympus camera (FIG. 17).

Wound Healing

Figure 18A:
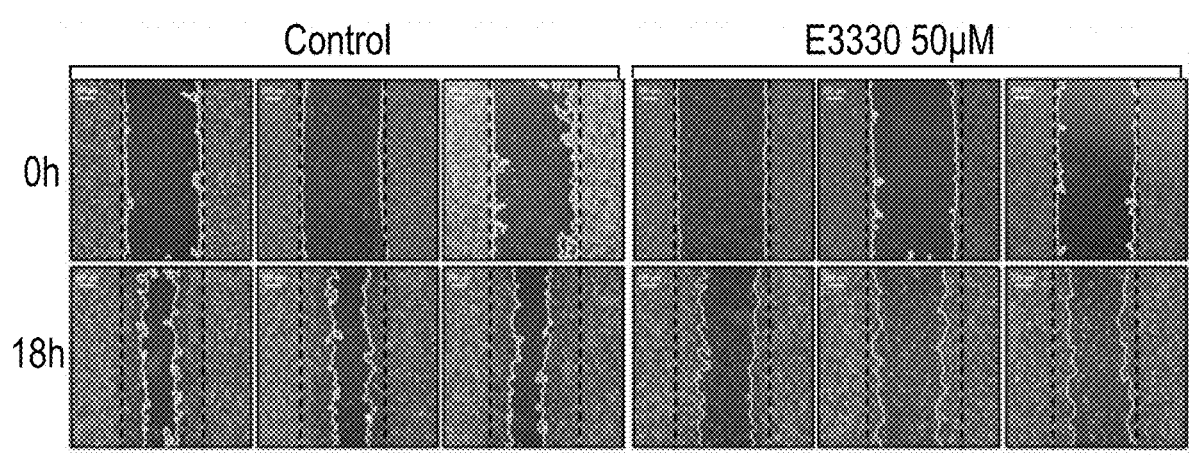
FIGS. 18A & 18B depict the effects of E3330 on wound closure of the ST8814 MPNST cell lines.
Figure 18B:
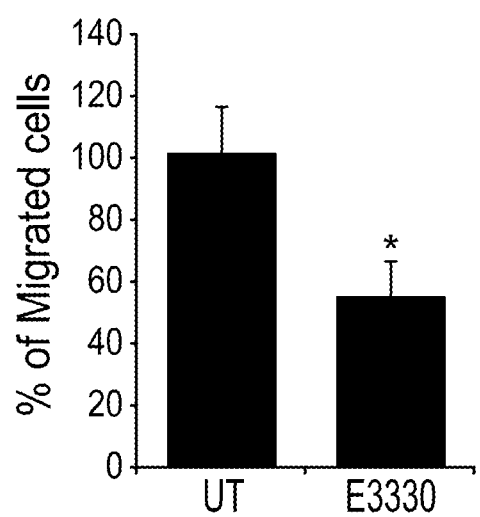
Figure 19A:
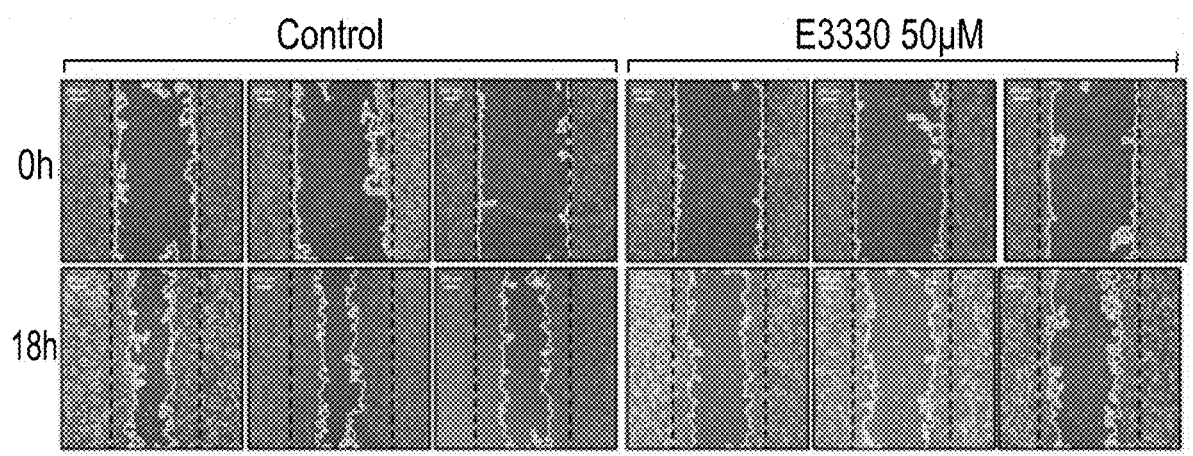
FIGS. 19A & 19B depict the effects of E3330 on wound closure of the S462 MPNST cell lines.
Figure 19B:
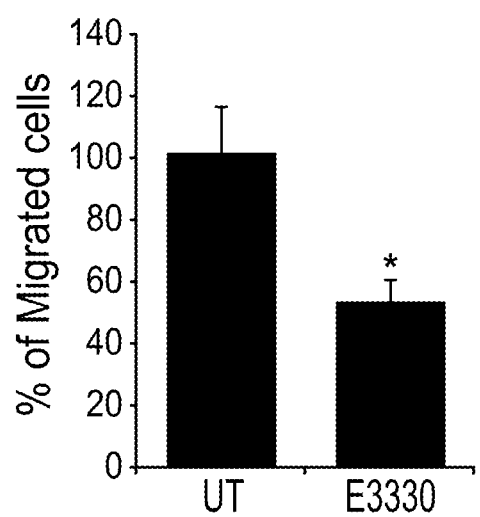

Cells were seeded in 35-mm plates and left to reach 80-90% confluency. Cells were then synchronized in 1% (v/v) FBS DMEM for 24 hours and "wounded" by scratching with a pipette tip. Dead cells were removed with PBS wash and then subsequently replaced with DMEM (10% (v/v) FBS). Cells were treated with 50 μM E3330 and placed in an incubator (5% $CO_2$/37° C.) for 18 hours. The scratched areas were measured using ImageJ. Pictures were taken before treatment and 18 hours after treatment using an inverted AMG EVOS microscope equipped with an Olympus camera (FIGS. 18A & 19A). Percentage of migrated cells was then calculated (FIGS. 18B & 19B). A T-test was performed using Prism to determine significance. 3 individual experiments were performed.

What is claimed is:

1. A method for inhibiting malignant peripheral nerve sheath tumors (MPNST) in a subject in need thereof, the method comprising administering to the subject an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1.

2. The method of claim 1 further comprising administering at least one additional therapeutic agent to the subject.

3. The method of claim 2 wherein the at least one additional therapeutic agent is selected from the group consisting of an inhibitor of signal transducer and activator of transcription 3 (STAT3), an inhibitor of carbonic anhydrase IX (CA9), an inhibitor of vascular endothelial growth factor receptor (VEGF-R), and combinations thereof, wherein when the additional therapeutic agent is a signal transducer and activator of transcription 3 (STAT3) inhibitor, the inhibitor is selected from the group consisting of 2-Hydroxy-4-(((4-methylphenyl)sulfonyloxy)acetyl) amino)-benzoic acid/S3I-201, 6-Nitrobenzo[b]thiophene-1, 1-dioxide/stattic, OCHROMYCINONE, 4-[[(4-cyclohexylphenyl)methyl][2-[methyl[(2,3,4,5,6-pentafluorophenyl) sulfonyl]amino]acetyl]amino]-benzoic acid (SH-4-54), 4-(N-(4-Cyclohexylbenzyl)-2-(2,3,4,5,6-pentafluoro-N-methylpenylsulfonamido)acetamido)-2-hydroxybenzoic acid (BP-1-102), PG-S3-001, PG-S2-002, PG-S3-003, and combinations thereof.

* * * * *